US012758264B2

(12) United States Patent
Bell

(10) Patent No.: US 12,758,264 B2
(45) Date of Patent: Oct. 13, 2026

(54) EXTERNAL FIXATOR, KIT COMPRISING THE SAME, AND METHOD OF FIXATION

(71) Applicant: KINGS TREE INNOVATIONS LIMITED, Cheshire (GB)

(72) Inventor: David Robert Bell, Greater Manchester (GB)

(73) Assignee: KINGS TREE INNOVATIONS LIMITED, Cheshire (GB)

( * ) Notice: Subject to any disclaimer, the term of this patent is extended or adjusted under 35 U.S.C. 154(b) by 59 days.

(21) Appl. No.: 18/291,650

(22) PCT Filed: Mar. 1, 2022

(86) PCT No.: PCT/IB2022/051786
§ 371 (c)(1),
(2) Date: Jan. 24, 2024

(87) PCT Pub. No.: WO2023/037169
PCT Pub. Date: Mar. 16, 2023

(65) Prior Publication Data

US 2025/0082367 A1 Mar. 13, 2025

(30) Foreign Application Priority Data

Sep. 7, 2021 (GB) ..................................... 2112724

(51) Int. Cl.
*A61B 17/64* (2006.01)
*A61B 17/88* (2006.01)
*A61B 17/00* (2006.01)

(52) U.S. Cl.
CPC ........ *A61B 17/645* (2013.01); *A61B 17/8897* (2013.01); *A61B 2017/00915* (2013.01)

(58) Field of Classification Search
CPC ... A61B 17/64; A61B 17/6425; A61B 17/645; A61B 17/88; A61B 17/8897; A61B 17/00
See application file for complete search history.

(56) References Cited

U.S. PATENT DOCUMENTS 6,565,563 B1 5/2003 Agee et al.
7,153,302 B1 12/2006 Hajianpour
(Continued)

FOREIGN PATENT DOCUMENTS

CN 102783998 A 11/2012
CN 109171844 A 1/2019
(Continued)

OTHER PUBLICATIONS

Ng, C.Y. & Oliver, C.W.: "Fractures of the Proximal Interphalangeal Joint of the Fingers", Journal of Bone & Joint Surgery (Jun. 2009), vol. 91-B, No. 6, pp. 705-712.
(Continued)

*Primary Examiner* — Christopher J Beccia
(74) *Attorney, Agent, or Firm* — Banner & Witcoff, Ltd.

(57) ABSTRACT

The present invention provides an external fixator (1) for fixation of a joint, such as a proximal interphalangeal (PIP) joint of a finger, and a kit comprising a congruent pair of such external fixators (1). The external fixator (1) comprises a rigid planar member made of a radio-transparent material. The planar member comprises a circular through hole (6) and a rectilinear main slot (10), which is radially aligned with the through hole (6). The external fixator (1) may also comprise a circular arc (8) of radio-opaque material centred on the through hole (6), a tail (14) to aid in its manipulation, and one or more subsidiary slots (20). The main and subsidiary slots (10, 20) have dentilated inner surfaces. In addition to a congruent pair of external fixators (1), the kit may further comprise a plurality of Kirschner wires and one or more stoppers (not shown). In use, the pair of external fixators are placed transversely on each lateral side of a patient's finger, a first one of the Kirschner wires is inserted through the through holes (6) in each external fixator (1) and through the condyle or head of the proximal phalanx. A
(Continued)

second one of the Kirschner wires is inserted through the main slot (10) in each external fixator (1) and through the middle phalanx. The third Kirschner wire is inserted through a convenient one of the subsidiary slots (20) in each external fixator (1) and through, over or under the middle phalanx or a fragment thereof. Movement of the second Kirschner wire along the main slots (10) in the direction of arrow D can be used to apply a distraction force to the joint. Movement of the third Kirschner wire along the one of the subsidiary slots (20) towards the main slot (10) can be used to reduce subluxation of the middle phalanx or a fragment thereof. The one or more stoppers, which engage with the dentilated inner surfaces of the main and subsidiary slots (10, 20), prevent backwards movement of the Kirschner wires along the main and/or subsidiary slots (10, 20) thereafter. The invention also provides a method which comprises providing a congruent pair of such external fixators (1) for use in a surgical operation.

23 Claims, 22 Drawing Sheets

(56) References Cited

U.S. PATENT DOCUMENTS

| | | | | |
|---|---|---|---|---|
| 7,717,916 | B2 | 5/2010 | Hajianpour | |
| 8,123,747 | B2 | 2/2012 | Hajianpour | |
| 8,246,561 | B1 | 8/2012 | Agee et al. | |
| 8,262,657 | B2 | 9/2012 | Hajianpour | |
| 8,377,061 | B1 | 2/2013 | Hajianpour | |
| 8,628,530 | B2 | 1/2014 | Hajianpour | |
| 2007/0055233 | A1 | 3/2007 | Brinker | |
| 2012/0029517 | A1 | 2/2012 | Tan | |
| 2014/0163570 | A1* | 6/2014 | Reynolds | A61B 17/1703 606/86 R |
| 2018/0028272 | A1* | 2/2018 | Tredinnick | A61B 17/1764 |
| 2018/0296246 | A1 | 10/2018 | Perret et al. | |

FOREIGN PATENT DOCUMENTS

| | | | |
|---|---|---|---|
| DE | 102018103566 | A1 | 8/2019 |
| EP | 0512792 | A1 | 11/1992 |
| GB | 2489471 | A | 10/2012 |
| WO | 2008-098016 | A2 | 8/2008 |
| WO | 2015-167581 | A1 | 11/2015 |

OTHER PUBLICATIONS

Suzuki, Y., Matsunaga, T., Sato, S. & Yokoi, T.: "The Pins and Rubbers Traction System for Treatment of Comminuted Intraarticular Fractures and Fracture-Dislocations in the Hand", Journal of Hand Surgery (Edinburgh, Scotland) (Feb. 1994), vol. 19, No. 1, pp. 98-107.

Hynes, M.C. & Giddins, G.E.: "Dynamic External Fixation for Pilon Fractures of the Interphalangeal Joints", Journal of Hand Surgery (Edinburgh, Scotland) (Apr. 2001), vol. 26, No. 2, pp. 122-124.

Robertson, R.C., Cawley, J.J. & Faris, A.M.: "Treatment of Fracture-Dislocation of the Interphalangeal Joints of the Hand", Journal of Bone Joint Surgery (1946), No. 28, pp. 68-70.

Schenck, R.R.: "Dynamic Traction and Early Passive Movement for Fractures of the Proximal Interphalangeal Joint", Journal of Hand Surgery [of America] (1986), No. 11, pp. 850-858.

May 11, 2022—International Search Report—Intl App PCT/IB2022/051786.

May 11, 2022—(WO) Written Opinion of ISA—Intl App PCT/IB2022/051786.

Jan. 13, 2022—(GB) Search Report—App GB2112724.6.

* cited by examiner

EXTERNAL FIXATOR, KIT COMPRISING THE SAME, AND METHOD OF FIXATION

CROSS REFERENCE TO RELATED APPLICATIONS

This is a U.S. National Phase Application under 35 U.S.C. § 371 of International Application No. PCT/IB2022/051786, filed Mar. 1, 2022, which claims priority to United Kingdom Application No. 2112724.6, filed Sep. 7, 2021, which was published Under PCT Article 21 (2), the entire contents of which are incorporated herein by reference.

The present invention concerns an external fixator for fixation of a fractured joint, a kit at least comprising a congruent pair of such external fixators, and a method of using a pair of such external fixators in a surgical operation. The external fixator of the invention is particularly suitable for fixation of a fractured joint in a digit (that is, in a finger or toe), such as the proximal interphalangeal (PIP) and distal interphalangeal (DIP) joints of the fingers, but may also be used, for example, for fixation of a fractured wrist joint, such as one presenting a die-punch injury.

BACKGROUND OF THE INVENTION

Proximal interphalangeal (PIP) joints are located in each of the fingers of the human hand between the condyle or head of the proximal phalanx (P1) and the base of the middle phalanx (P2). Distal interphalangeal (DIP) joints are located in each of the fingers of the human hand between the condyle or head of the middle phalanx (P2) and the base of the distal phalanx (P3). PIP and DIP joints may sustain one of several different fracture injuries requiring surgical intervention. These fracture injuries include subluxation of bones and bone fragments in both dorsal (back of the hand) and volar (palm of the hand) directions, pilon fractures, compression of one or more bone fragments and even gross comminution of bone. The aims of managing such fractures are to reduce subluxation and dislocation of bones and bone fragments, and to restore joint congruity as far as possible. These aims can be met in several different ways, depending on the configuration of the fracture and the degree of bone fragmentation.

A common surgical technique which is used to manage such injuries is ligamentotaxis. In ligamentotaxis, a distraction (pulling apart) force is applied to the fractured joint. When the distraction is applied, collateral ligaments and other soft tissues around the joint tighten and help to pull any attached bone fragments into alignment.

Several devices exist in the prior art to apply distraction to a PIP joint. In order for the distraction to be applied to the fractured joint, such a device must be mechanically connected to the joint on both proximal and distal sides of the fracture. This is typically achieved by passing a Kirschner wire (K-wire) transversely through the finger on each of the proximal and distal sides of the fracture, and then applying the distraction force to the inserted K-wires.

A first known device for applying the distraction force to the inserted K-wires is the Allison device, described in Ng, C. Y. & Oliver, C. W.: "Fractures of the Proximal Interphalangeal Joint of the Fingers", *Journal of Bone & Joint Surgery* (June 2009), Vol. 91-B, No. 6, pp. 705-12. In the Allison device, a pair of torsion springs are placed under tension and attached to the K-wires on the proximal and distal sides of the fracture to push the K-wires apart. This device has several disadvantages as follows. Firstly, the Allison device is difficult to adjust. Secondly, the Allison device cannot be used to correct any subluxation or to realign compressed bone fragments. Thirdly, the distraction force applied by the torsion springs to the K-wires depends on the amount by which the torsion springs are initially tensioned and cannot be easily controlled.

A second known device is the Suzuki frame, described in Suzuki, Y., Matsunaga, T., Sato, S. & Yokoi, T.: "The Pins and Rubbers Traction System for Treatment of Comminuted Intraarticular Fractures and Fracture-Dislocations in the Hand", *Journal of Hand Surgery* (Edinburgh, Scotland) (February 1994), Vol. 19, No. 1, pp. 98-107. In the Suzuki frame, a long proximal K-wire is bent perpendicularly at both ends to finish distal of the distal K-wire. Hooks are bent on to the ends of both the proximal and distal K-wires, and then a pair of elastic bands are stretched between and attached to the hooks on the proximal and distal K-wires on each lateral side of the finger to pull the K-wires apart. The distraction force can be controlled by adjusting the number of twists and/or loops in each elastic band. However, this control is not precise. A third K-wire may also be inserted transversely to correct subluxation. However, this correction of subluxation is not dynamic or adjustable, without removing and reinserting the third K-wire into a new position. Thirdly, the Suzuki frame cannot be used to correct the central fragment of a pilon fracture.

A third known device is the Hynes and Giddins device, described in Hynes, M. C. & Giddins, G. E.: "Dynamic External Fixation for Pilon Fractures of the Inter-Phalangeal Joints", *Journal of Hand Surgery* (Edinburgh, Scotland) (April 2001), Vol. 26, No. 2, pp. 122-124. In the Hynes and Giddins device, the proximal and distal K-wires are bent into a Z-shape to push against each other. The distraction force can be controlled by adjusting the angle of the Z shape in the wire arms. However, this control is not precise. A third K-wire may also be inserted transversely to correct subluxation. However, the Hynes and Giddins device suffers from the same disadvantages as the Suzuki frame, in that correction of subluxation is not dynamic or adjustable, without removing and reinserting the third K-wire into a new position and that it cannot be used to correct the central fragment of a pilon fracture.

Another known device is the "Banjo" splint, which was originally described in Robertson, R. C., Cawley, J. J. & Faris, A. M.: "Treatment of Fracture-Dislocation of the Interphalangeal Joints of the Hand", *Journal of Bone Joint Surgery* (1946), No. 28, pp. 68-70. The "Banjo" splint has also been modernised in Schenck, R. R.: "Dynamic Traction and Early Passive Movement for Fractures of the Proximal Interphalangeal Joint", *Journal of Hand Surgery* [of America] (1986), No. 11, pp. 850-858. However, the Banjo splint is cumbersome due it is large external frame and cannot be used to correct any subluxation or to realign compressed bone fragments, for example in a pilon fracture.

Other prior art devices are also described in U.S. Pat. Nos. 6,565,563; 8,246,561 B, both assigned to John M. Agee, US 2012/0029517 A of Virak Tan, and EP 0 512 792 A of Smith & Nephew Richards, Inc.

Further prior art is described in CN 109171844 A, GB 2 489 471 A and CN 102783998 A. CN 109171844 A describes an osteotomy device used in tibial osteotomy and femoral osteotomy with functions of spreading and fixing bone sutures. GB 2 489 471 A describes a finger fixator which comprises a two-part elongate strut element and two pin-engagable elements spaced apart on the two-part elongate strut element. The two-part elongate strut element includes spacing-adjustment means for selectively adjusting and setting a spacing between the two pin-engagable elements. The spacing adjustment means may take the form of a rotatable member or a releasable sliding or telescopic mechanism. The strut element may have spaced apart arcuate arms for receiving the pins. CN 102783998 A describes a hinged traction external fixation device, which comprises two parallel screws, a rotating central pin, a maintaining reset pin, a fixing dragging pin and nuts.

OBJECT OF THE INVENTION

An object of the present invention, therefore, is to provide an improved external fixator for fixation of a fractured joint, a kit which at least comprises a pair of such external fixators, and a method of using a pair of such external fixators in a surgical operation.

DESCRIPTION OF THE INVENTION

Accordingly, in a first aspect, the present invention provides an external fixator for fixation of a fractured joint. The fixator comprises a rigid planar member having a pair of parallel opposite sides. The planar member comprises a circular through hole normal to the parallel opposite sides and a rectilinear main slot connecting the parallel opposite sides with each other. The main slot is radially aligned with the through hole, and has a dentilated inner surface.

As used herein, the term "external" means external to the body of a patient. Such an external fixator has the following advantages. Taking an example, in which the external fixator is used for fixation of a proximal interphalangeal (PIP) joint, the circular through hole of the external fixator provides a drill guide for inserting a first Kirschner wire through the condyle or head of the proximal phalanx P1 by firstly marking the skin of the patient through the through hole with a dot and then inserting the first Kirschner wire transversely through the head of P1 at the location of the dot.

Once the first Kirschner wire has been thus inserted, a second Kirschner wire may then also be inserted transversely into the middle phalanx P2 at a convenient location distal to the fracture complex and taking care to ensure that the second Kirschner wire is parallel to the first Kirschner wire. An external fixator of the invention can then be threaded over the first and second Kirschner wires, one on each lateral side of the finger, by passing the first Kirschner wire through the circular through hole and the second Kirschner wire through the main slot of each external fixator. A distraction force may than be applied to the PIP joint by increasing the separation between the first and second Kirschner wires, by moving the second Kirschner wire along the main slot in a direction away from the through hole.

The dentilated inner surface of the main slot has the advantage that it acts as a ratchet, helping to control the application of this distraction force and to prevent the second Kirschner wire from sliding back in a direction towards the through hole. Once the required amount of distraction force has been applied, the second Kirschner wire may then be locked in place. This may be done, for example, by inserting a stopper into the main slot on the side of the second Kirschner wire which is nearer to the through hole or by bonding the second Kirschner wire to the planar member, or both. Alternatively or additionally, another Kirschner wire, pin or screw which is thicker than a width of the main slot may be inserted into the main slot on the side of the second Kirschner wire which is nearer to the through hole, thus eating into the planar member on either side of the main slot where this thicker Kirschner wire, pin or screw is inserted. Since this thicker Kirschner wire, pin or screw is thicker than the main slot, it is unable to slide along the main slot in either direction. The exposed ends of the first and second Kirschner wires, as well as of the thicker Kirschner wire, pin or screw, if one is used, can then be bent out of the way and/or cut down in size.

Moreover, the external fixator of the invention has the advantage that it can also be used to realign a bone fragment which is impacted distally into the middle phalanx P2 by inserting another Kirschner wire through the main slot in the external fixator, between the impacted bone fragment and the middle phalanx P2. If this other Kirschner wire is then moved along the main slot in a direction towards the through hole in the external fixator, whilst the second Kirschner wire holds the middle phalanx P2 in place relative to the proximal phalanx P1, this movement of the other Kirschner wire pushes the bone fragment towards the head of the proximal phalanx P1 and brings it back into alignment.

Advantageous embodiments of the present invention may be configured according to any claim and/or part of the following description.

In some embodiments, the dentilated inner surface of the main slot may comprise a first plurality of dentilations, each tapering in a direction along the main slot which is away from the through hole. This has the advantage that such dentilations provide a ratchet hindering movement of a Kirschner wire inserted through the main slot in a direction towards the through hole. The Kirschner wire may thus be held in the main slot to apply a distraction force to P2.

In some embodiments, the rigid planar member may be made of a radio-transparent material and the external fixator may further comprise a circular arc of radio-opaque material centred on the through hole. Making the rigid planar member of a radio-transparent material allows X-ray imaging of a fractured joint which is subject to fixation, through the rigid planar member. Providing the external fixator with such an arc of radio-opaque material has the advantage that it provides a guide, allowing the circular through hole of the fixator to be aligned with the centre of rotation of the condyle or head of the proximal phalanx P1 by carefully aligning the arc of radio-opaque material with an outline of the head of the proximal phalanx P1, as they both appear on an X-ray image. When positioned in this fashion, the skin of the patient can be marked through the circular through hole of the external fixator with a dot to represent the centre of rotation of the head of P1.

In some embodiments, the rigid planar member may further comprise a subsidiary slot connecting the parallel opposite sides with each other, wherein the subsidiary slot extends away from the through hole, oblique to the main slot, and has a dentilated inner surface. The addition of such a subsidiary slot has the advantage that the external fixator may then also be used to reduce subluxation of the middle phalanx P2 or a fragment thereof, as well as to apply a distraction force to a PIP joint. Because the subsidiary slot is oblique to the main slot, movement of a Kirschner wire along the subsidiary slot can be used to apply a correspondingly oblique force to the middle phalanx P2 or a fragment thereof. The dentilated inner surface of the subsidiary slot has the advantage that it acts as a ratchet, helping to control the movement of the Kirschner wire and to prevent it from sliding back in a direction opposite to its direction of movement.

In some embodiments, the dentilated inner surface of the subsidiary slot may comprise a second plurality of dentilations, each tapering in a direction along the subsidiary slot which is towards the main slot. This has the advantage that such dentilations provide a ratchet hindering movement of a Kirschner wire inserted through the subsidiary slot in a direction towards the main slot.

The subsidiary slot may be curved. If so, the direction of curvature is preferably towards an opposite end of the main slot from the through hole. Preferably however, the subsidiary slot is rectilinear. This has the advantage that the amount of force which can be applied to the middle phalanx P2 or a fragment thereof by movement of a Kirschner wire along the subsidiary slot may be controlled more easily.

In some embodiments, the rigid planar member may comprise a plurality of the subsidiary slots arranged parallel to each other. This has the advantage that the plurality of subsidiary slots provides a corresponding plurality of different locations for insertion of a Kirschner wire through, over or under the middle phalanx P2 or a fragment thereof, thereby allowing its subluxation to be corrected in a wide range of different fractures.

In some embodiments, the rigid planar member may comprise two such pluralities of said subsidiary slots, wherein each of the two pluralities of subsidiary slots is arranged on opposite sides of the main slot, the two pluralities of subsidiary slots are reflection-symmetric with each other about a line, and the main slot lies on the line. This has the advantage that one of the pluralities of subsidiary slots may be used to reduce a dorsal subluxation of the middle phalanx P2 or a fragment thereof and the other of the pluralities of subsidiary slots may be used to reduce a volar subluxation of the middle phalanx P2 or a fragment thereof at the same time.

In some embodiments, the dentilated inner surface of the main slot may comprise a third plurality of dentilations, located closer to the through hole than the first plurality of dentilations and each tapering in a direction along the main slot which is towards the through hole. This has the advantage that such dentilations provide a ratchet hindering movement of a Kirschner wire inserted through the main slot in a direction away from the through hole. The Kirschner wire may thus be held in the main slot in a position which realigns a bone fragment in a pilon fracture in a direction towards the through hole, that is towards the head of the proximal phalanx P1, at the same time as another Kirschner wire applies a distraction force to P2 in the opposite direction by means of the first plurality of dentilations.

In some embodiments, the rigid planar member may have a shape which is reflection-symmetric about a longitudinal axis, wherein the through hole and the main slot lie on the longitudinal axis. If so, this has the advantage that the rigid planar member is not chiral, so does not have a preferred right way round, and may therefore be used on either side of a finger which is subject to fixation of a PIP joint without having to be firstly oriented the right way round, thereby saving time during surgery.

If the rigid planar member has a shape which is reflection-symmetric as just described and the external fixator further comprises an arc of radio-opaque material, in some embodiments, each end of the arc may define a line which subtends an angle with the longitudinal axis, which lies in a range of angles from 100 to 140 degrees, inclusive. This has the advantage that if the external fixator is rotated through the same angle out of alignment with a joint which is subject to fixation, the arc will then be brought into alignment with the outline of the condyle or head of the proximal phalanx P1 in an X-ray image, but the external fixator can still be easily manipulated by a surgeon without obstructing the X-ray image.

If the rigid planar member has a shape which is reflection-symmetric as just described, the shape of the rigid planar member may be any one of oblong, elliptical, oval, ovate, obovate, spatulate, rhomboidal and deltoid. These preferred shapes have the advantage that one of them can be chosen to conform to the shape of the tip of a finger which is subject to fixation of a PIP joint, which helps in alignment of the fixator with the finger during surgery.

Alternatively, the rigid planar member may comprise a tail located at an opposite end of the main slot from the through hole. Such a tail has the advantage that it provides a handle which may be used by a surgeon to hold and manipulate the fixator during surgery. In particular, since it is desirable to avoid exposure of the surgeon's fingers to X-rays during radiography of a patient through the rigid planar member, the tail provides a handle by which the fixator may be manipulated using an instrument, such as an artery clip or haemostat. On the other hand, since the tail does not conform to the shape of the tip of a finger which is subject to fixation of a PIP joint, there is no risk that such manipulation of the fixator will interfere with the finger.

If the rigid planar member does comprise such a tail, preferably the tail has a deltoid or bifurcate shape and comprises a flat or concave surface at an opposite end of the rigid planar member from the through hole. This has the advantage that the flat or concave surface provides a convenient surface which a surgeon can push against when moving a Kirschner wire along the main slot in a direction away from the through hole, in order to hold the external fixator in place as the Kirschner wire is moved relative to the fixator. Furthermore, if the tail does have such a deltoid or bifurcate shape, then overall, the rigid planar member takes on the appearance of a fish, with the through hole and main slot respectively taking on the appearance of an eye and backbone of the fish, and if one or more subsidiary slots are present in the rigid planar member as well, other bones of the fish radiating out from the backbone. This fish-like appearance has the advantage that it can help to speed up identification of parts of the fixator when training surgeons in its use, and also to avoid miscommunication and thereby save time during surgery.

In some embodiments, the arc of radio-opaque material may be embedded within and enclosed by the rigid planar member. This has the advantage that if the radio-opaque material comprises, for example, a metal, whereas the rigid planar member is, for example, an inert plastics material, the radio-opaque material may be protected from corrosion by the rigid planar member, and conversely, there is no risk of the radio-opaque material interacting with other surgical elements (such as a Kirschner wire) or with the finger of the patient or other externalities once the fixator has been installed, for example if the patient is allergic to certain metals. In other embodiments, however, the arc of radio-opaque material may instead be provided as an insert within the planar member, for ease of manufacture.

In a second aspect, the present invention also provides a kit comprising a congruent pair of external fixators as described herein. As used herein, the term "congruent" is used to mean that the pair of external fixators are geometrically congruent with each other. Such a kit has the advantage that it provides a pair of external fixators having the same shape and size as each other, which may therefore be positioned on both lateral sides of a finger which is subject to fixation of a PIP joint.

In some embodiments, the pair of external fixators in the kit may bear different indicia and/or have different colours from each other. This has the advantage that the external fixators are then distinguishable from each other by their different indicia and/or colours, which allows a surgeon to quickly and easily identify to a colleague which one of the two fixators they are referring to, thereby saving time during surgery.

In some embodiments, the kit may further comprise a plurality of Kirschner wires, wherein a first one of the Kirschner wires has a diameter which fits through the through hole in each of the pair of external fixators, and a second one of the Kirschner wires has a diameter which fits through the main slot in each of the pair of external fixators, but is restrained by the dentilated inner surfaces of the main slots from sliding freely along the main slots. This has the advantage that the pair of external fixators are provided with Kirschner wires which are of the correct size to be used with the pair of external fixators.

If the kit does comprise such a plurality of Kirschner wires, the sharp ends of the Kirschner wires in the kit may each be provided with a respective cap to protect persons handling the wires from the sharp ends. Each such cap may take the form of soft silicone tubing, a rubber bung, or the like.

Preferably, the main slot has a width which is the same as the diameter of the through hole in the external fixators. This has the advantage that the first and second Kirschner wires may then also have the same diameter as each other and may therefore be used interchangeably.

In some embodiments, the kit may further comprise a stopper adapted to engage with the dentilated inner surface of the main slot in each of the pair of external fixators. Such a stopper has the advantage that it can be used to prevent a Kirshner wire from sliding along the main slot in a direction opposite to that in which the Kirschner wire has been moved in order to apply a force to an anatomical element of a joint.

In some embodiments, if the rigid planar member of each of the pair of external fixators further comprises a subsidiary slot, the kit may further comprise a third one of the Kirschner wires having a diameter which fits through the subsidiary slots, but is restrained by the dentilated inner surfaces of the subsidiary slots from sliding freely along the subsidiary slots. This has the advantage that the pair of external fixators is provided with a Kirschner wire which is of the correct size to be used in the subsidiary slots thereof.

Preferably, the subsidiary slot has a width which is the same as the width of the main slot and as the diameter of the through hole in the external fixators. This has the advantage that the third Kirschner wire may then have the same diameter as the first and second Kirschner wires and may therefore be used interchangeably with them.

If the rigid planar member of each of the pair of external fixators further comprises a subsidiary slot, in some embodiments, the kit may further comprise a stopper adapted to engage with the dentilated inner surface of the subsidiary slot in each of the pair of external fixators. Such a stopper has the advantage that it can be used to prevent a Kirshner wire from sliding along the subsidiary slot in a direction opposite to that in which the Kirschner wire has been moved in order to apply a force to an anatomical element of a PIP joint.

In some embodiments, the stopper may comprise a cruciform head having arms joined to each other by circular arcs, and a body attached to the head, wherein the body has a maximum width equal to a maximum separation between the respective dentilated inner surfaces of the main and subsidiary slots. Such a stopper has the advantage that the shape of the head engages with the circular cross-section of a cylindrical Kirschner wire, whereas the cylindrical body forms a friction fit with a respective one of the main and subsidiary slots.

Alternatively or additionally, the stopper may be made of a thermoplastic material. Such a stopper has the advantage that it can be bonded to the planar member in a desired location by applying heat to the stopper, for example using an instrument like a diathermy or electrocautery device, until the stopper melts.

In some embodiments, the kit may further comprise a container of adhesive for bonding at least one of the Kirschner wires to at least one of the pair of external fixators. The container may, for example, be a sachet or tube. The adhesive may, for example, be an epoxy resin or polystyrene cement, and of medical grade.

In some embodiments, the kit may further comprise a Kirschner wire, pin or screw having a diameter which is greater than a width of the main slot in each of the pair of external fixators. Such a thicker Kirschner wire, pin or screw may be used to lock the position of one or more other Kirschner wires in place by inserted it into the main slot, since once inserted, the thicker Kirschner wire, pin or screw will be unable to slide along the main slot in either direction.

In some embodiments, the thicker Kirschner wire, pin or screw may bear different indicia and/or have a different colour from any other Kirschner wires in the kit, thereby allowing a surgeon to quickly and easily distinguish it from the other Kirschner wires.

In some embodiments, the kit may further comprise a pair of wire benders and/or wire cutters for bending and/or cutting at least one of the Kirschner wires. The wire benders and/or wire cutters may be reusable following suitable sterilization, rather than being disposable, so that, for example, a pair of wire benders and/or wire cutters may only be included with, for example, 1 in every 5 such kits supplied to the same surgeon or hospital.

In a third aspect, the present invention also provides a method which comprises providing a congruent pair of external fixators as described herein for use in a surgical operation.

The method may further comprise: inserting a first Kirschner wire having a diameter which fits through the through hole in each of the pair of external fixators transversely through the condyle of a first bone proximal to a fracture complex; inserting a second Kirschner wire having a diameter which fits through the main slot in each of the pair of external fixators, but is restrained by the dentilated inner surfaces of the main slots from sliding freely along the main slots, transversely through a second bone distal to the fracture complex and parallel to the first Kirschner wire; threading a first one of the congruent pair of external fixators over the first and second Kirschner wires on a first lateral side of the fracture complex, by passing the first Kirschner wire through the circular through hole and the second Kirschner wire through the main slot of the first external fixator; threading a second one of the congruent pair of external fixators over the first and second Kirschner wires on a second, opposing lateral side of the fracture complex, by passing the first Kirschner wire through the circular through hole and the second Kirschner wire through the main slot of the second external fixator; applying a distraction force to the fracture complex by increasing the separation between the first and second Kirschner wires, by moving the second Kirschner wire along the main slots of each of the congruent pair of external fixators in a direction away from the through hole of each respective one of the congruent pair of external fixators; and locking the second Kirschner wire in place on each of the congruent pair of external fixators by at least one of: inserting a stopper into the main slot on the side of the second Kirschner wire which is nearer to the through hole than the second Kirschner wire; bonding the second Kirschner wire to the rigid planar member; and inserting a pin or screw which is thicker than a width of the main slot into the main slot on the side of the second Kirschner wire which is nearer to the through hole than the second Kirschner wire.

In some embodiments, if the fracture complex comprises a bone fragment which is subject to subluxation, wherein the rigid planar member of each of the congruent pair of external fixators further comprises a subsidiary slot connecting the parallel opposite sides of the rigid planar member with each other, the subsidiary slot extends away from the through hole, oblique to the main slot of each of the rigid planar members, and has a dentilated inner surface, the method may further comprise: inserting a third Kirschner wire having a diameter which fits through the subsidiary slot in each of the pair of external fixators, but is restrained by the dentilated inner surfaces of the subsidiary slots from sliding freely along the subsidiary slots, transversely through the subsidiary slot in each of the pair of external fixators and through the bone fragment subject to subluxation, parallel to the first and second Kirschner wires; reducing the subluxation of the bone fragment by moving the third Kirschner wire in a direction towards the main slot of each respective one of the congruent pair of external fixators; and locking the third Kirschner wire in place on each of the congruent pair of external fixators by at least one of: inserting a stopper, pin or screw into the subsidiary slot on the side of the third Kirschner wire which is further from the main slot than the third Kirschner wire; and bonding the third Kirschner wire to the rigid planar member.

In some embodiments, if the fracture complex comprises a bone fragment impacted distally to the condyle of the first bone, the method may further comprise: inserting a fourth Kirschner wire having a diameter which fits through the main slot in each of the pair of external fixators, but is restrained by the dentilated inner surfaces of the main slots from sliding freely along the main slots, transversely through the main slot in each of the pair of external fixators, between the impacted bone fragment and the second bone, parallel to the first and second Kirschner wires; moving the fourth Kirschner wire along the main slots of each of the congruent pair of external fixators in a direction towards the through hole of each respective one of the congruent pair of external fixators; and locking the fourth Kirschner wire in place on each of the congruent pair of external fixators by at least one of: inserting a stopper, pin or screw into the main slot on the side of the fourth Kirschner wire which is further from the through hole than the fourth Kirschner wire; and bonding the fourth Kirschner wire to the rigid planar member.

In some embodiments, wherein the rigid planar member of at least one of the congruent pair of external fixators is made of a radio-transparent material, and the at least one of the congruent pair of external fixators comprises a circular arc of radio-opaque material centred on the through hole of the respective one of the external fixators, the method may further comprise aligning the through hole of the at least one of the congruent pair of external fixators with the centre of rotation of the condyle of the first bone by aligning the arc of radio-opaque material with an outline of the condyle of the first bone, as they both appear on an X-ray image, and marking the skin of the patient through the through hole of the at least one of the congruent pair of external fixators with the centre of rotation of the condyle of the first bone.

BRIEF DESCRIPTION OF THE DRAWINGS

Further features and advantages of the present invention will become apparent from the following detailed description, which is given by way of example and in association with the accompanying drawings, in which.

DETAILED DESCRIPTION

Figure 1:
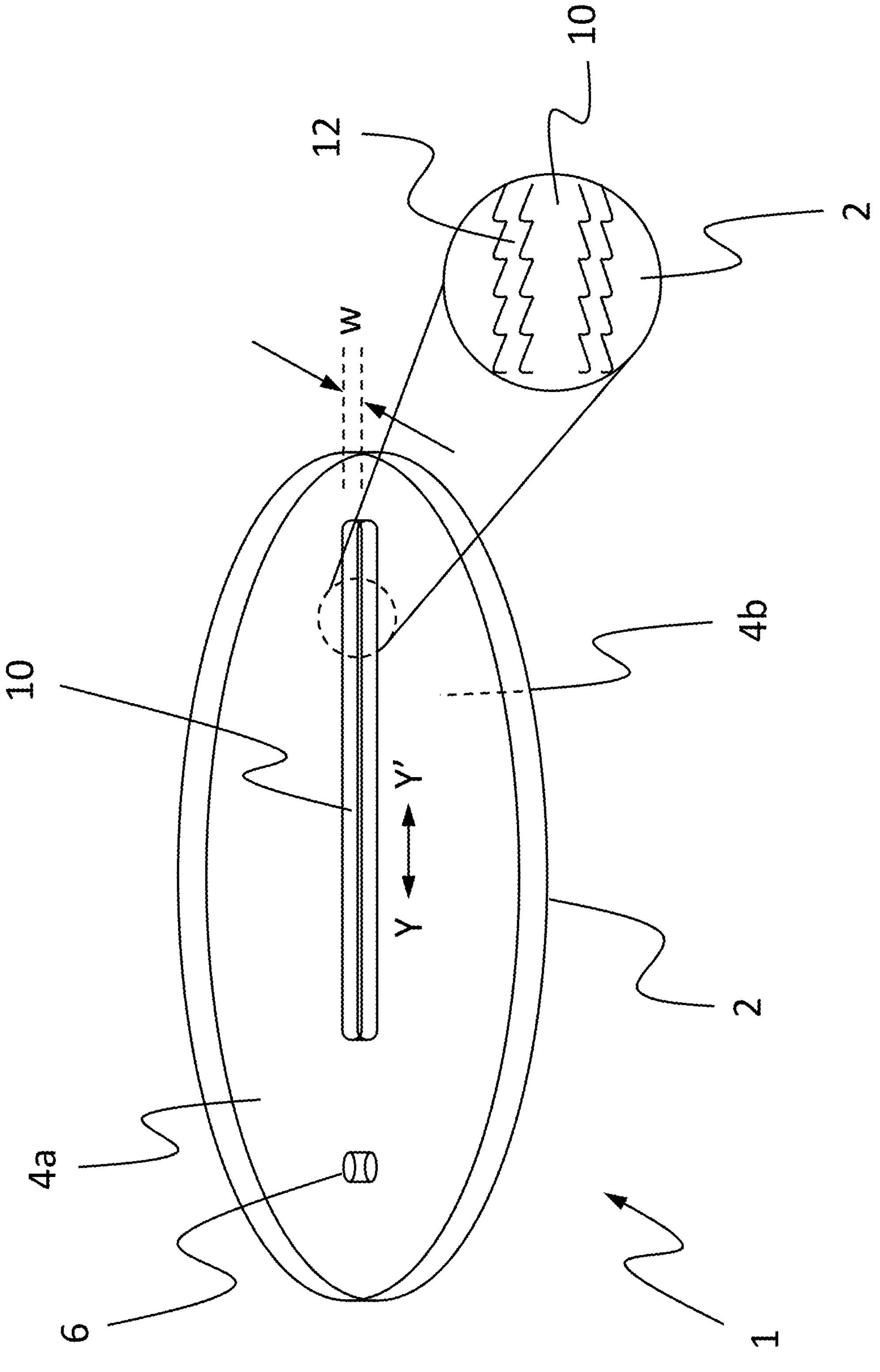
FIG. 1 is a schematic perspective view of a first embodiment of an external fixator.

FIG. 1 schematically shows a first embodiment of an external fixator 1 for fixation of a joint. The external fixator 1 comprises a rigid planar member 2 of radio-transparent material, in other words, material which is transparent to X-rays, allowing radiography of a patient through the planar member 2. For example, the planar member 2 may be made of a stiff plastics material manufactured by injection moulding. The plastics material may comprise an antimicrobial additive, such as a silver compound. The planar member 2 has a pair of parallel opposite sides 4*a*, 4*b*, which in this embodiment, give the external fixator 1 an elliptical shape. The planar member 2 comprises a circular through hole 6 and a rectilinear main slot 10. The through hole 6 is oriented normal to the parallel opposite sides 4*a*, 4*b* of the planar member 2 and the main slot 10 connects the parallel opposite sides 4*a*, 4*b* with each other. Thus a rectilinear rod or wire passed through the through hole 6 or the main slot 10 will adopt an orientation perpendicular to the parallel opposite sides 4*a*, 4*b* of the planar member 2.

FIG. 1 also schematically shows an enlargement of the main slot 10. The main slot 10 is radially aligned with the through hole 6. As the enlargement of FIG. 1 shows, the main slot 10 has a pair of opposing inner surfaces 12, which are both dentilated, corrugated or serrated. Thus, a rectilinear rod or wire passed through the main slot 10 is restrained by the pair of dentilated inner surfaces 12 of the main slot 10 from sliding freely along the main slot 10 in the direction indicated by the arrows Y-Y'. The ability of the rectilinear rod or wire to slide along the main slot 10 will depend on the diameter of the rod or wire relative to the width, w, of the main slot 10. If the rod or wire has a diameter which is only slightly less than the width, w, of the main slot 10, then the rod or wire may be enabled to slide along the main slot 10 by being pushed strongly enough in the direction indicated by the arrows Y-Y' to induce a slight flexure of the rigid planar member 2, thereby easing the dentilated inner surfaces 12 of the main slot 10 slightly apart from each other and temporarily increasing the width, w, of the main slot 10 by a small amount by elastic deformation of the planar member 2. If, on the other hand, the rod or wire has a diameter which is considerably less than the width, w, of the main slot 10, then the ability of the rod or wire to slide along the main slot 10 will nonetheless be impeded by the dentilated inner surfaces 12. For example, the main slot 10 may have a width, w, of about 1.2 mm, designed to accommodate a rod or wire having a diameter of 1.1. mm. Preferably, the width, w, of the main slot 10 should be substantially the same as the diameter of the through hole 6, so that rods or wires of the same diameter as each other can be passed through both the through hole 6 and the main slot 10.

Figure 2:
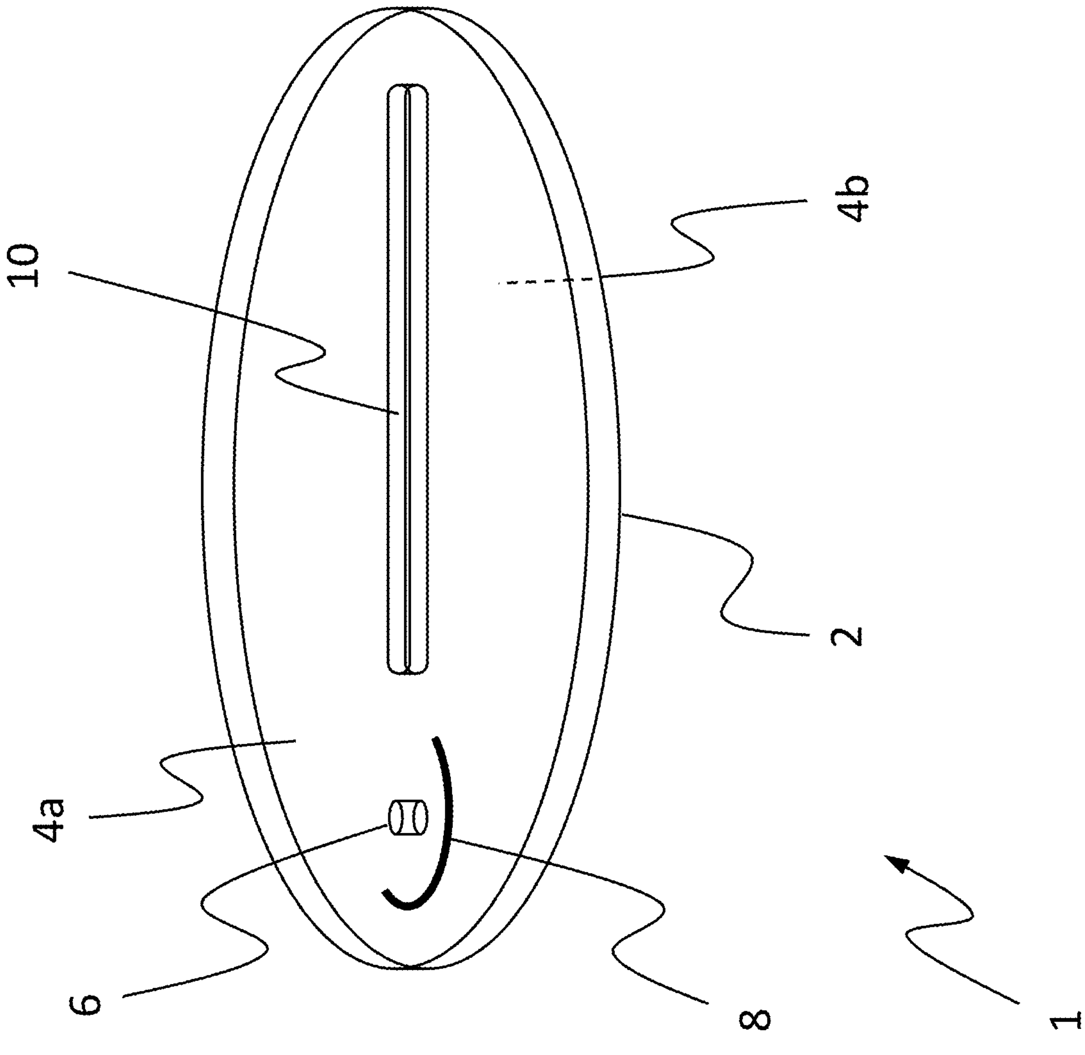
FIG. 2 is a schematic perspective view of a second embodiment of an external fixator.

FIG. 2 schematically shows a second embodiment of an external fixator 1 for fixation of a joint. The external fixator 1 of FIG. 2 is in all respects the same as that shown in FIG. 1, except that it further comprises a semicircular arc 8 of radio-opaque material centred on the through hole 6. Since the semicircular arc 8 is made of radio-opaque material, it will show up on an X-ray image during radiography of a patient through the rigid planar member 2. For example, the arc 8 may be made of a metal or metal alloy, such as stainless steel. In this embodiment, the arc 8 is embedded within and enclosed by the planar member 2. Although in this embodiment, the arc 8 is shown as being a semicircle, the arc 8 may be any portion of the circumference of a circle from as little as about 45 degrees up to and including a complete circle. Moreover, whereas the semicircular arc 8 in the embodiment of FIG. 2 is shown as being continuous, in other possible embodiments, it may be discontinuous, in the manner of a dashed and/or dotted line. Finally, whereas in the embodiment of FIG. 2, the arc 8 is shown as being of finite width, the arc 8 may instead be an inner or outer arcuate edge of a more extended piece of radio-opaque material, provided that the piece of radio-opaque material is not so extensive as to obstruct X-ray imaging of other anatomical elements of a patient.

Preferably, if the external fixator 1 is intended for fixation of a fractured PIP joint, the arc 8 should have a radius roughly equal to the average radius of the condyle or head of the proximal phalanx (P1) in the finger of an adult human. However, this is not strict. For example, an arc 8 of smaller radius will be more appropriate for fixation of a PIP joint in the finger of a child. A range of external fixators 1 comprising arcs 8 of different radii may conveniently be provided for fixation of PIP joints in different patients.

In the embodiment of FIG. 2, the arc 8 is positioned and oriented within the external fixator 1 as shown in FIG. 2, so that if the external fixator 1 is longitudinally aligned with the middle phalanx P2 of a patient's finger, obstruction of any possible fragment of P2 in the case of a pilon fracture by the arc 8 is avoided when taking an X-ray image. On the other hand, if the fixator 1 is rotated out of alignment with P2, anticlockwise about the through hole 6 through an angle of approximately 100 to 140 degrees, the arc 8 will then be brought into alignment with the outline of the condyle or head of the proximal phalanx P1 in an X-ray image. Thus, with the fixator 1 in such an orientation, the fixator 1 may be accurately attached through the centre of the condyle of P1 by inserting a rectilinear rod or wire through the through hole 6. Then by rotating the fixator 1 clockwise through approximately the same angle, back into alignment with P2 again, the fixator 1 can also be attached to the middle phalanx P2 by inserting another rectilinear rod or wire through the main slot 10, without the X-ray image of P2 being obstructed by the arc 8.

Figure 3:
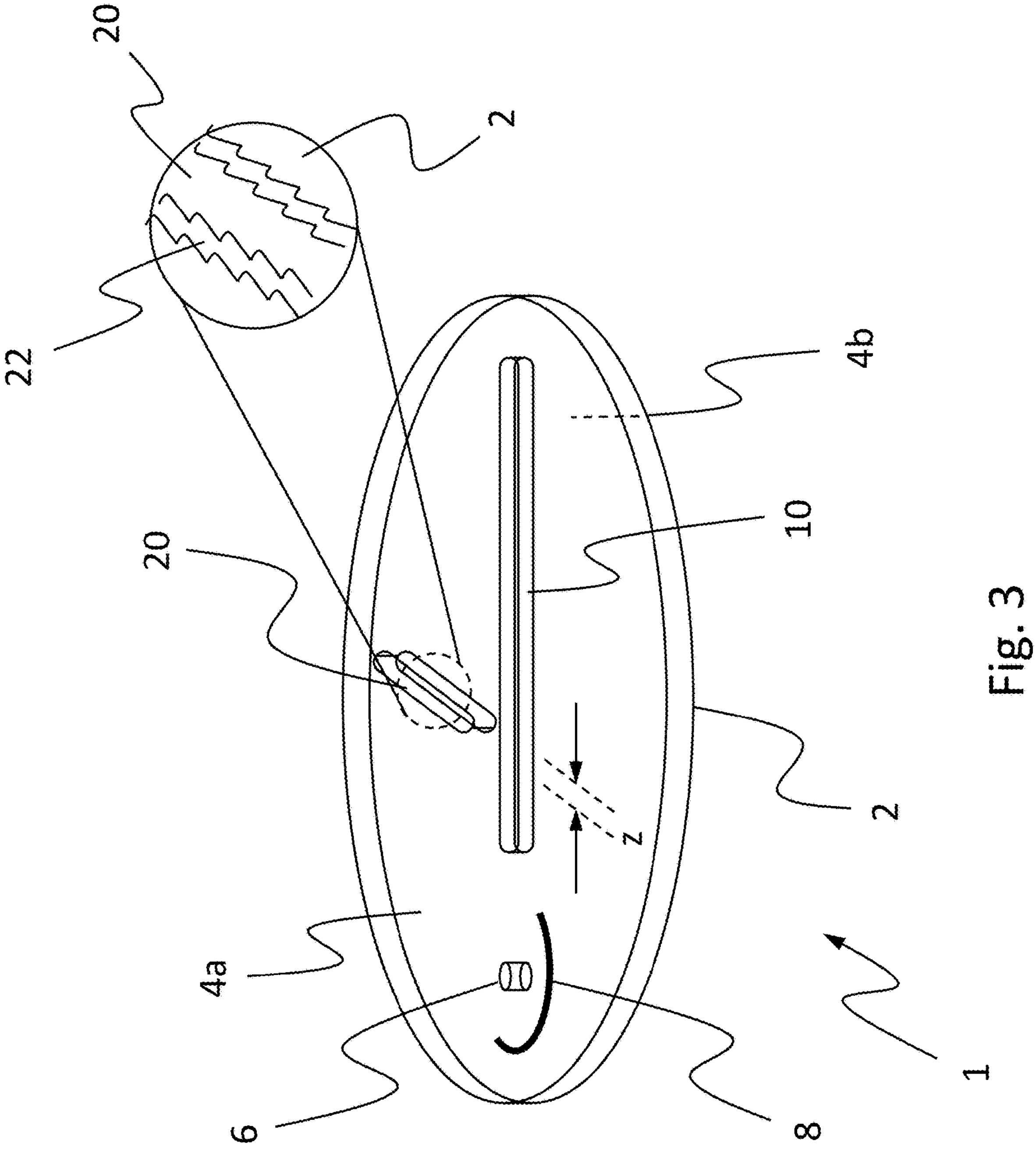
FIG. 3 is a schematic perspective view of a third embodiment of an external fixator.

FIG. 3 schematically shows a third embodiment of an external fixator 1 for fixation of a joint. The external fixator 1 of FIG. 3 is in all respects the same as the external fixator 1 of FIG. 2, except that the rigid planar member 2 further comprises a subsidiary slot 20 connecting the parallel opposite sides 4*a*, 4*b* of the planar member 2 with each other. As shown in FIG. 3, the subsidiary slot 20 extends away from the through hole 6, at an oblique angle to the main slot 10. Like the main slot 10, the subsidiary slot 20 has a pair of opposing inner surfaces 22, which are both dentilated, corrugated or serrated, as shown in the enlargement of the subsidiary slot 20 also contained in FIG. 2. Similar comments apply to subsidiary slot 20 in relation to a rectilinear rod or wire which is passed through the subsidiary slot 20 as were made above in relation to a rectilinear rod or wire passed through the main slot 10. Preferably, the width, z, of the subsidiary slot 20 is the same as the width, w, of the main slot 10 and the dentilated inner surfaces 22 of the subsidiary slot 20 have the same shape and size as the dentilated inner surfaces 12 of the main slot 10. If so, a rectilinear rod or wire of the same diameter as a rectilinear rod or wire passed through the main slot 10 can be passed through the subsidiary slot 20 and will behave in the same manner as the rod or wire passed through the main slot 10.

The subsidiary slot 20 can have any convenient shape and length. For example, the subsidiary slot 20 may be curved.

However, the subsidiary slot 20 is preferably rectilinear, as in the embodiment shown in FIG. 3.

Figure 4:
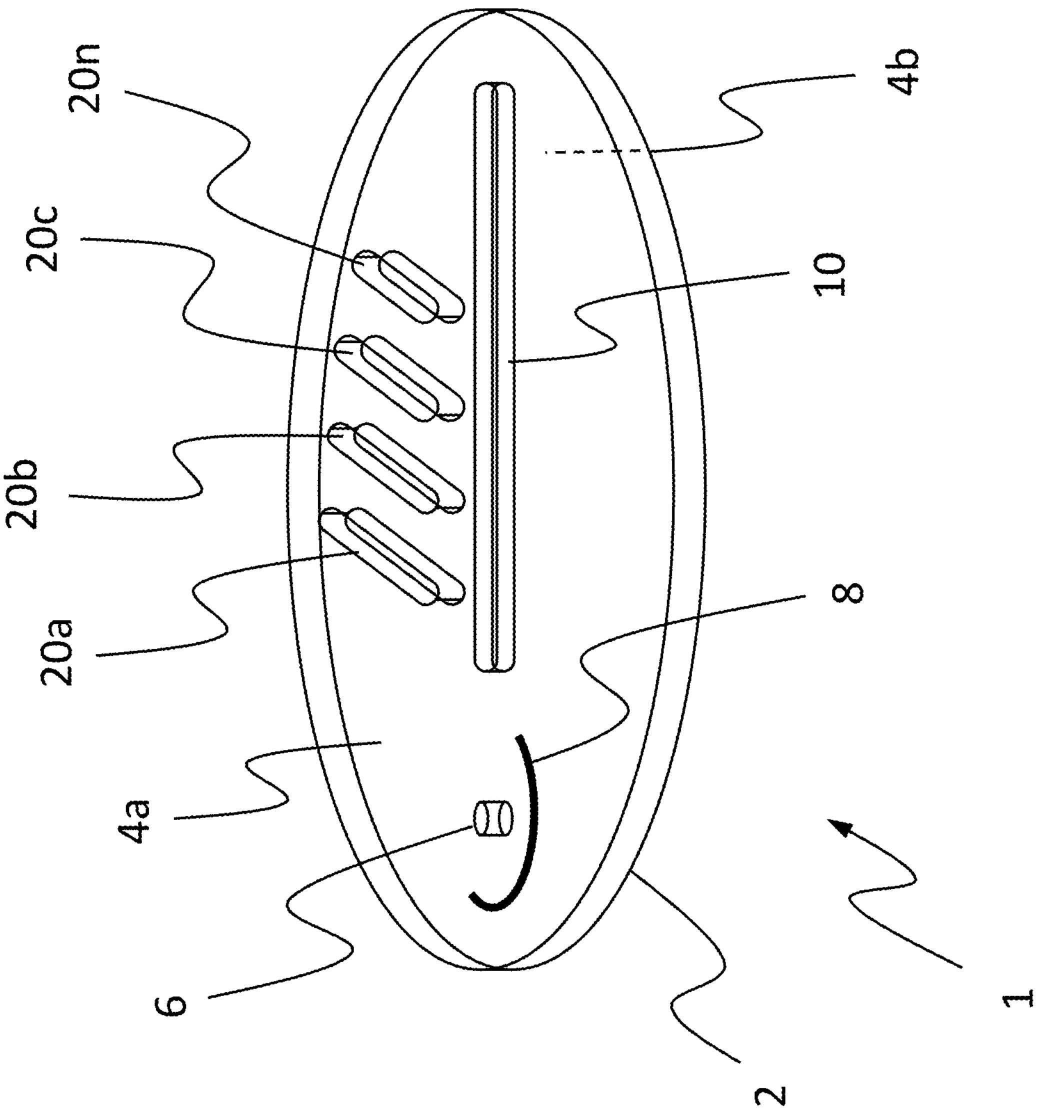
FIG. 4 is a schematic perspective view of a fourth embodiment of an external fixator.

FIG. 4 schematically shows a fourth embodiment of an external fixator 1 for fixation of a joint. The external fixator 1 of FIG. 4 is in all respects the same as the external fixator 1 of FIG. 2, except that it further comprises a plurality of the subsidiary slots 20*a*, 20*b*, 20*c*, . . . , 20*n* of the same type as shown and described above in relation to FIG. 3. In other words, each of the plurality of subsidiary slots 20*a*, 20*b*, 20*c*, . . . , 20*n* has a respective pair of opposing inner surfaces 22, which are both dentilated, corrugated or serrated.

The plurality of subsidiary slots 20*a*, 20*b*, 20*c*, . . . , 20*n* are arranged parallel to each other. However, the number of subsidiary slots 20*a*, 20*b*, 20*c*, . . . , 20*n* is not fixed and their spacing need not be regular. There can be any convenient number of subsidiary slots 20*a*, 20*b*, 20*c*, . . . , 20*n* and they can have any convenient spacing between an adjacent pair of them. For example, in the embodiment shown in FIG. 4, the plurality of subsidiary slots 20*a*, 20*b*, 20*c*, . . . , 20*n* are four in number and are spaced at regular intervals.

Furthermore, the plurality of subsidiary slots 20*a*, 20*b*, 20*c*, . . . , 20*n* need not have the same length as each other. Indeed, their lengths may be adapted to suit the shape of the external fixator 1. However, their widths are preferably the same as each other and also the same as the width of the main slot 10, so that a rectilinear rod or wire of the same diameter may be passed through any one of the plurality of subsidiary slots 20*a*, 20*b*, 20*c*, . . . , 20*n* and will behave in the same manner as if passed through another one of the plurality of subsidiary slots 20*a*, 20*b*, 20*c*, . . . , 20*n* or through the main slot 10.

Figure 5:
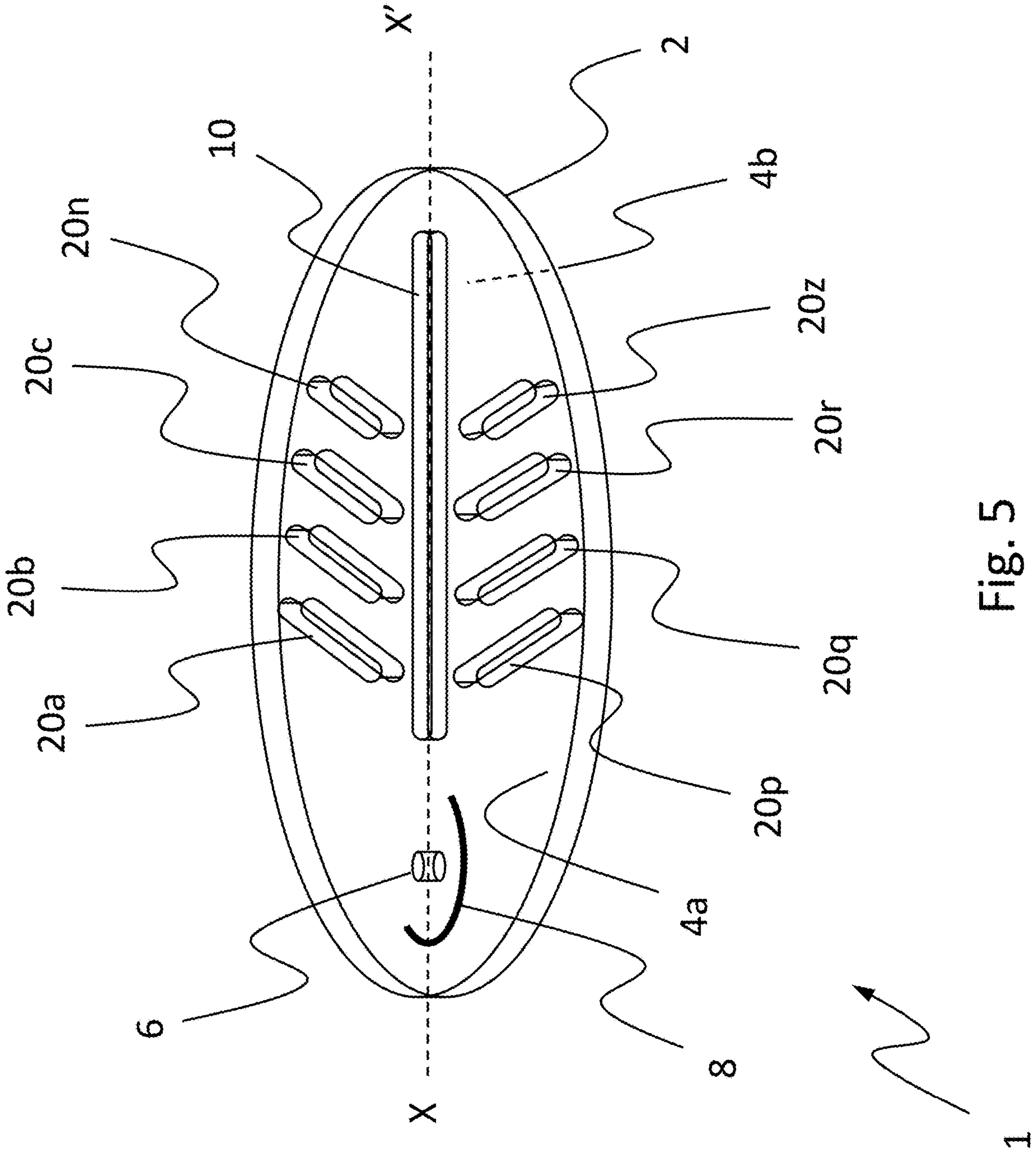
FIG. 5 is a schematic perspective view of a fifth embodiment of an external fixator.

FIG. 5 schematically shows a fifth embodiment of an external fixator 1 for fixation of a joint. The external fixator 1 of FIG. 5 is in all respects the same as the external fixator 1 of FIG. 4, except that the rigid planar member 2 comprises two pluralities of the subsidiary slots, 20*a*, 20*b*, 20*c*, . . . , 20*n* and 20*p*, 20*q*, 20*r*, . . . , 20*z* as shown and described above in relation to FIG. 3. Each of the two pluralities of subsidiary slots 20*a*, . . . , 20*n* and 20*p*, . . . , 20*z* is arranged on opposite sides of the main slot 10. The two pluralities of subsidiary slots 20*a*, . . . , 20*n* and 20*p*, . . . , 20*z* are reflection-symmetric with each other about a line X-X', on which the main slot 10 lies.

Figure 6:
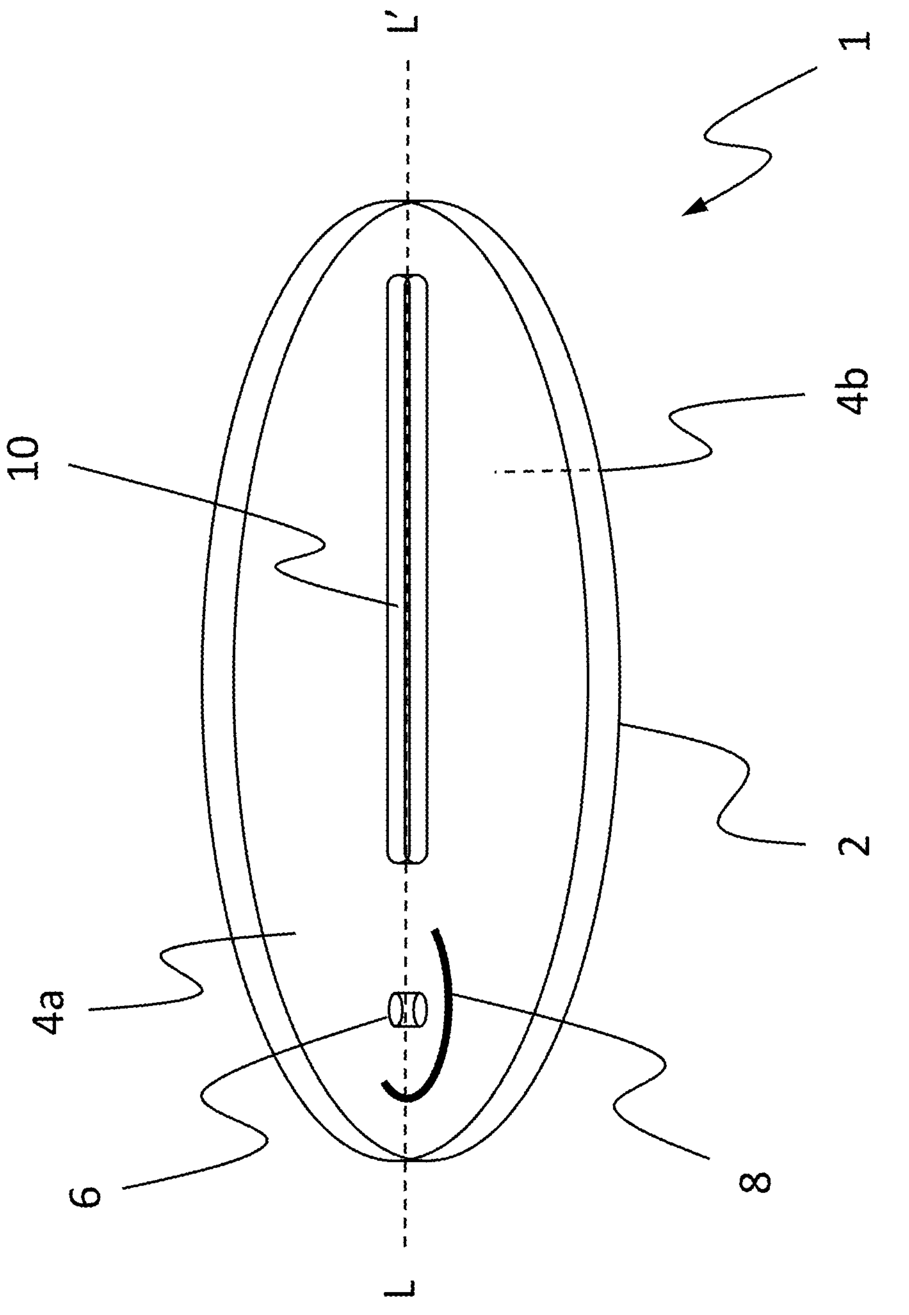
FIG. 6 is a schematic perspective view of a sixth embodiment of an external fixator.
Figure 7A:
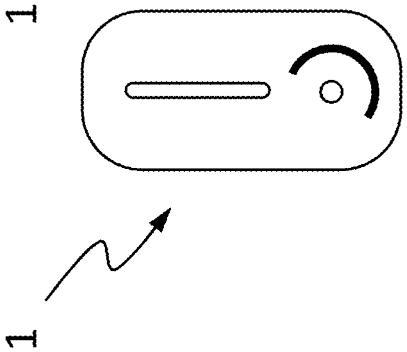
FIGS. 7A to 7H are schematic top plan views of a plurality of different embodiments of an external fixator.
Figure 7B:
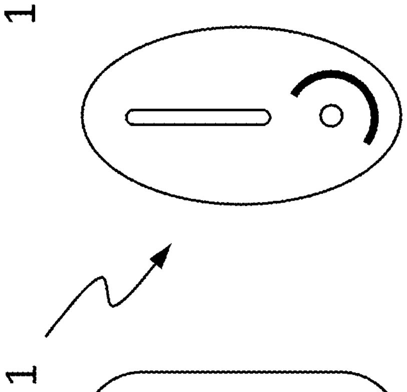
Figure 7C:
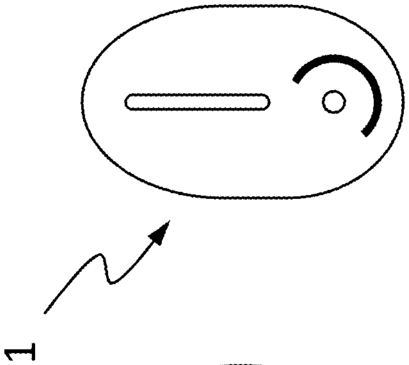
Figure 7D:
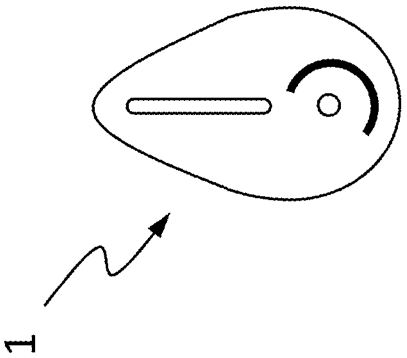
Figure 7E:
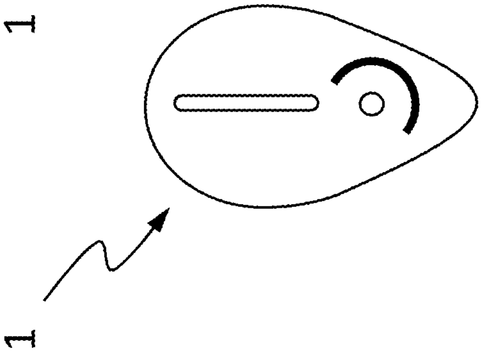
Figure 7F:
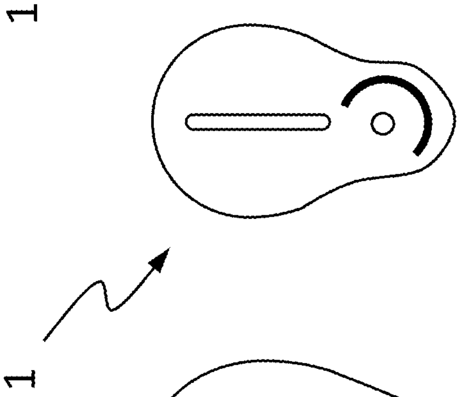
Figure 7G:
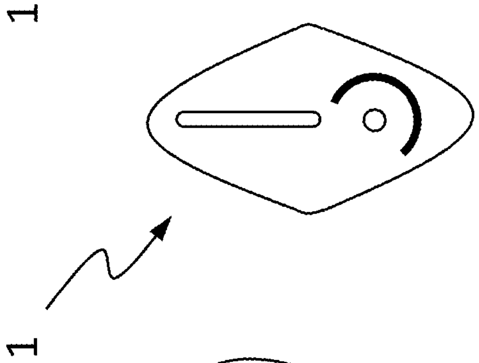
Figure 7H:
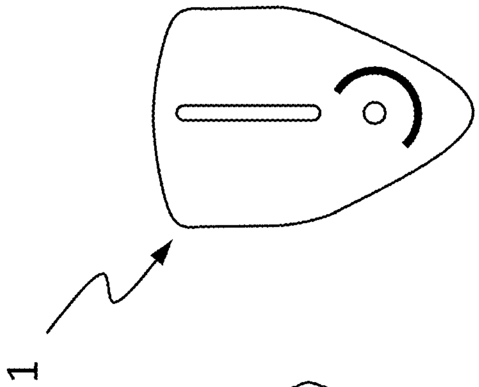

An external fixator 1 according to the present invention may be of any size. A range of different sizes to suit a range of differently sized digits of different patients may conveniently be provided. For example, a smaller sized external fixator 1 may be used for fixation of a joint in a child's finger or toe than in the corresponding finger or toe of an adult. The planar member 2 of an external fixator 1 according to the present invention may also have any shape. In other words, the outline or boundary of the planar member 2 may have any convenient form, provided that the rigid member 2 is flat. The shape of the planar member 2 may be adapted during manufacture to suit the shape of whichever joint on which the external fixator 1 is intended to be used for ligamentotaxis. Preferably, however, as in the sixth embodiment of an external fixator 1 shown in FIG. 6, the planar member 2 has a shape which is reflection-symmetric about a longitudinal axis L-L', and the through hole 6 and the main slot 10 lie on the longitudinal axis L-L'.

FIGS. 7A to 7H show a plurality of different embodiments of an external fixator 1 which conform to this preferred shape. FIGS. 7A to 7H respectively show embodiments of the external fixator 1, in which the shape of the planar member 2 is oblong, elliptical, oval, ovate, obovate, spatulate, rhomboidal and deltoid. The ovate and obovate forms only differ in that the orientation of the outline or boundary of the planar member 2 is reversed with respect to the positions of the through hole 6, the arc 8 of radio-opaque material and the main slot 10 in the planar member 2.

Figure 8:
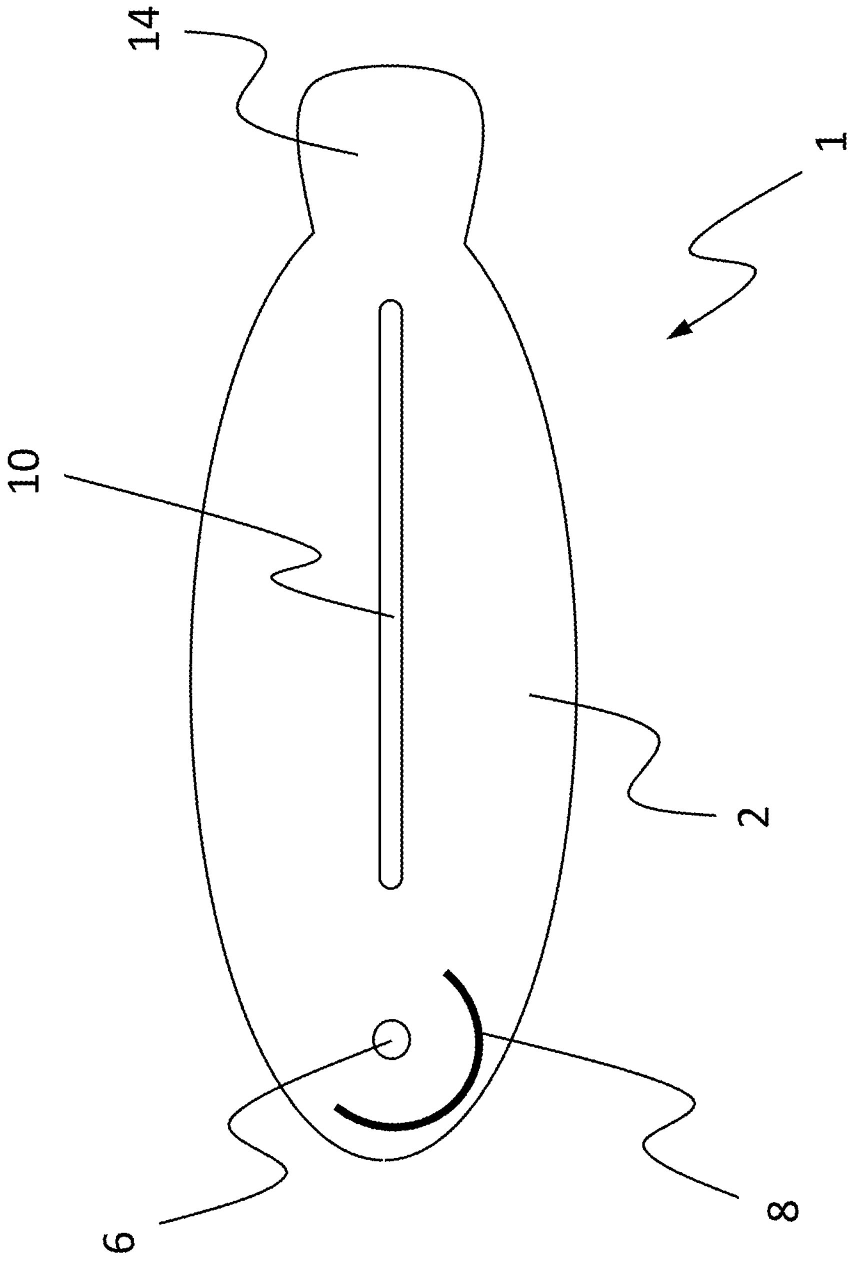
FIG. 8 is a schematic perspective view of a seventh embodiment of an external fixator.
Figure 9:
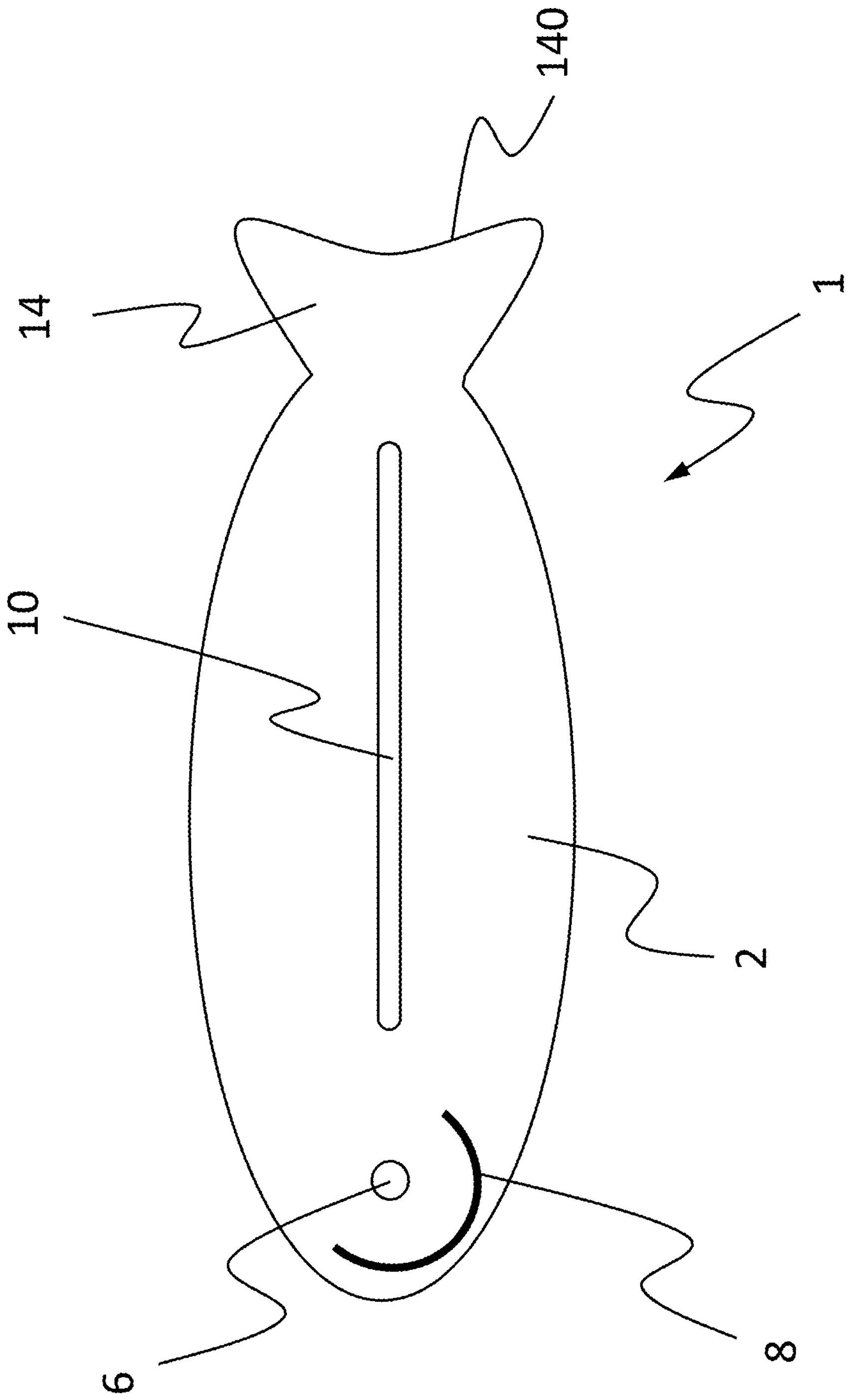
FIG. 9 is a schematic perspective view of a eighth embodiment of an external fixator.

FIG. 8 schematically shows a seventh embodiment of an external fixator 1 for fixation of a joint. The external fixator 1 of FIG. 8 is in all respects the same as the external fixator 1 of FIG. 2, except that the planar member 2 comprises a tail 14 located at an opposite end of the main slot 10 from the through hole 6. The tail 14 provides a handle which makes the external fixator 1 easier to hold and/or manipulate during surgery. The tail 14 may have a deltoid or bifurcate shape and comprise a flat or concave surface 140 at an opposite end of the planar member 2 from the through hole 6, as in the eighth embodiment of an external fixator 1 shown in FIG. 9. The surface 140 can be used by a surgeon to push against when moving a Kirschner wire along the main slot 10 in a direction away from the through hole 6, thereby holding the fixator 1 in place as the Kirschner wire moves relative to the fixator. Furthermore, a tail 14 with such a shape gives the fixator 1 the overall appearance of a fish. This has the advantage that it can be used to help speed up the identification of parts of the fixator 1 during surgery, as well as during training of surgeons in its use.

Figure 10:
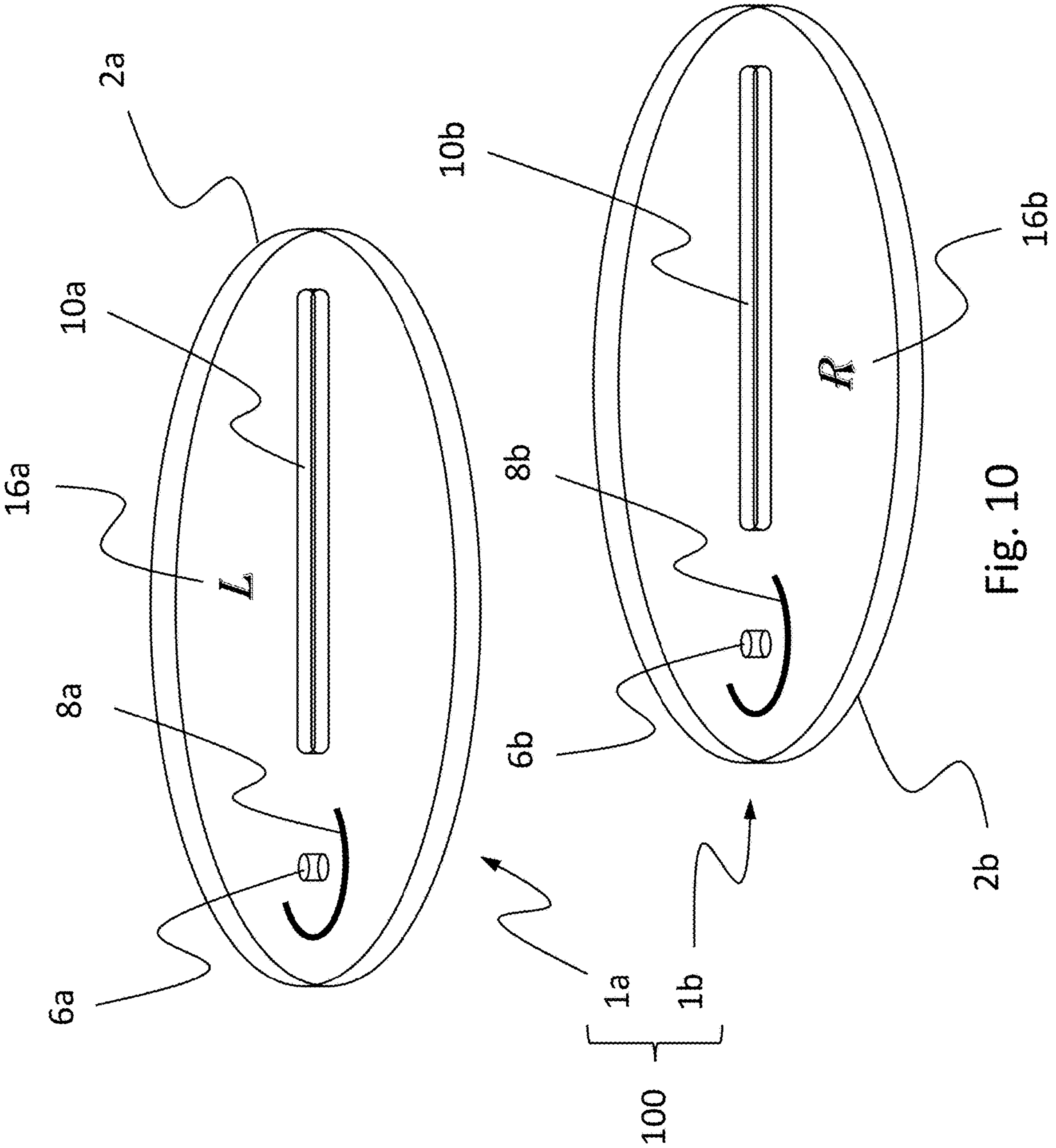
FIG. 10 is a schematic perspective view of a first embodiment of a kit comprising two external fixators.

FIG. 10 schematically shows a first embodiment of a kit 100 comprising a congruent pair of external fixators 1*a*, 1*b*. In other words, the kit 100 comprises a pair of external fixators 1*a*, 1*b*, which have the same shape and size as each other. This includes that the circular through holes, 6*a*, 6*b*, the arcs 8*a*, 8*b* of radio-opaque material and the main slots 10*a*, 10*b* have the same shape and size as each other, and not just that the outlines or boundaries of the planar members 2*a*, 2*b* have the same shape and size as each other. Each one of the congruent pair of external fixators 1*a*, 1*b* can be of any type according to the invention, including the embodiments of external fixators 1 already described above in relation to any of FIGS. 1 to 9. However, in the embodiment shown in FIG. 10, the pair of external fixators 1*a*, 1*b* also bear different indicia 16*a*, 16*b* from each other, which allow the pair of external fixators 1*a*, 1*b* to be distinguished from each other. For example, the different indicia 16*a*, 16*b* may be "L" and "R", respectively denoting left and right ones of the pair of external fixators 1*a*, 1*b*. Alternatively or additionally, the pair of external fixators 1*a*, 1*b* may have different colours from each other. In use, the pair of external fixators 1*a*, 1*b* are placed transversely on each lateral side of a patient's finger in the same orientation as each other, and with one of the parallel opposite sides 4*a*, 4*b* of a first one 1*a* of the external fixators facing one of the parallel opposite sides 4*a*, 4*b* of the second one 1*b* of the external fixators. Thus the different indicia 16*a*, 16*b* and/or different colours of the pair of external fixators 1*a*, 1*b* can be used by a surgeon to quickly and easily identify to a colleague which one of the two fixators they are referring to.

Figure 11:
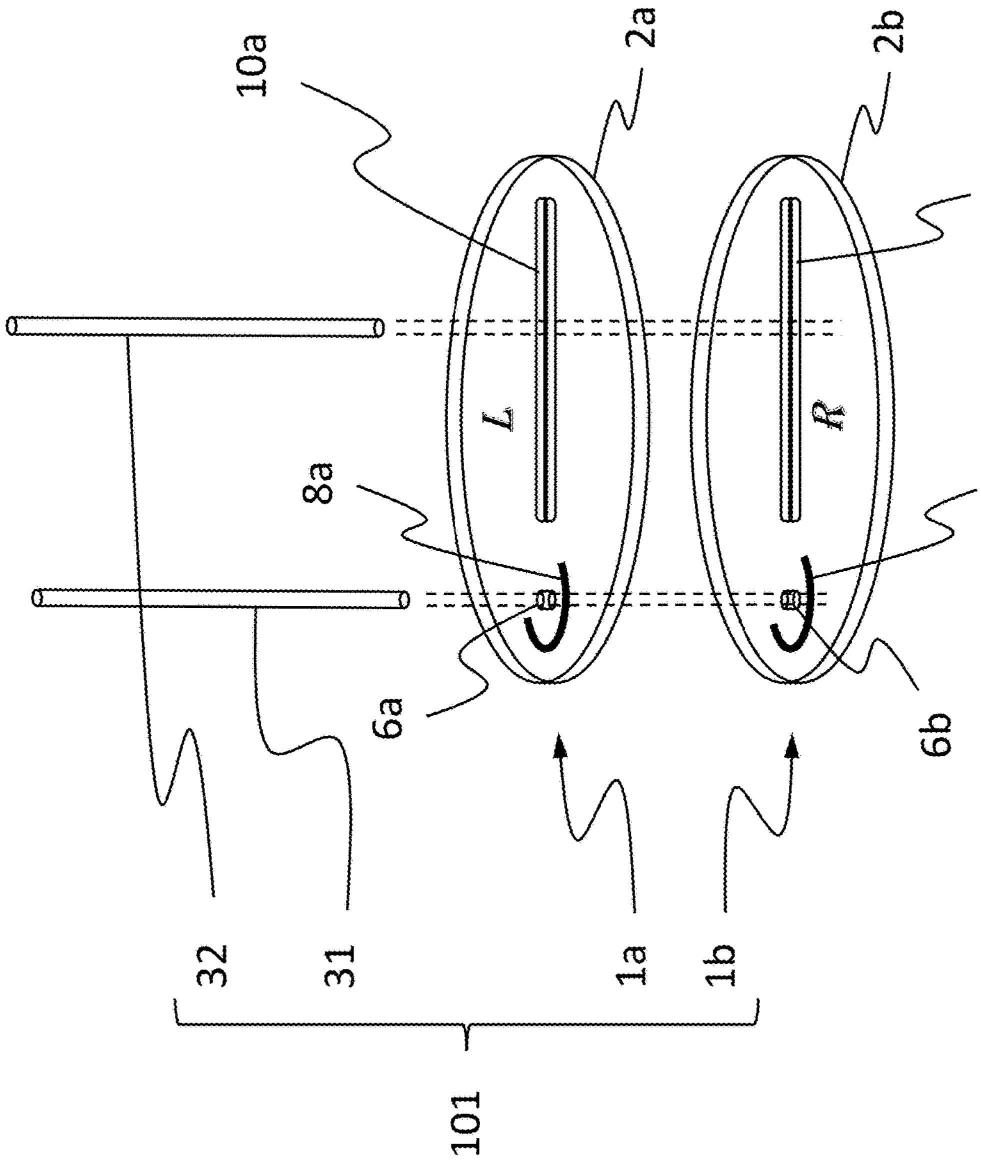
FIG. 11 is a schematic perspective view of a second embodiment of a kit comprising two external fixators and a plurality of Kirschner wires.

FIG. 11 schematically shows a second embodiment of a kit 101 comprising such a congruent pair of external fixators 1*a*, 1*b* and two Kirschner wires 31, 32. A first one 31 of the Kirschner wires has a diameter which fits through the through hole 6*a*, 6*b* in each of the pair of external fixators 1*a*, 1*b*. A second one 32 of the Kirschner wires has a diameter which fits through the main slot 10*a*, 10*b* in each of the pair of external fixators 1*a*, 1*b*, but is restrained by the dentilated inner surfaces 12*a*, 12*b* of the main slots 10*a*, 10*b* from sliding freely along the main slots 10*a*, 10*b*, in the manner described above in relation to FIG. 1. If the width of the main slots 10*a*, 10*b* is the same as the diameter of the through holes 6*a*, 6*b*, the diameter of the first one 31 of the Kirschner wires may be the same as the diameter of the second one 32 of the Kirschner wires.

In use, a patient's finger is interposed between the congruent pair of external fixators 1*a*, 1*b*. The first Kirschner wire 31 is inserted through the through hole 6*a* of a first one 1*a* of the pair of external fixators, through the head of the proximal phalanx P1 of the patient's finger and through the through hole 6*b* of the second one 1*b* of the pair of external fixators. The second Kirschner wire 32 is inserted through the main slot 10*a* in the first one 1*a* of the pair of external fixators, through the middle phalanx P2 of the patient's finger and through the main slot 10*b* in the second one 1*b* of the pair of external fixators. In order to apply a distraction force to the PIP joint between P1 and P2, the second Kirschner wire 32 is moved along the main slots 10*a*, 10*b* in a direction away from the through holes 6*a*, 6*b*.

Figure 12:
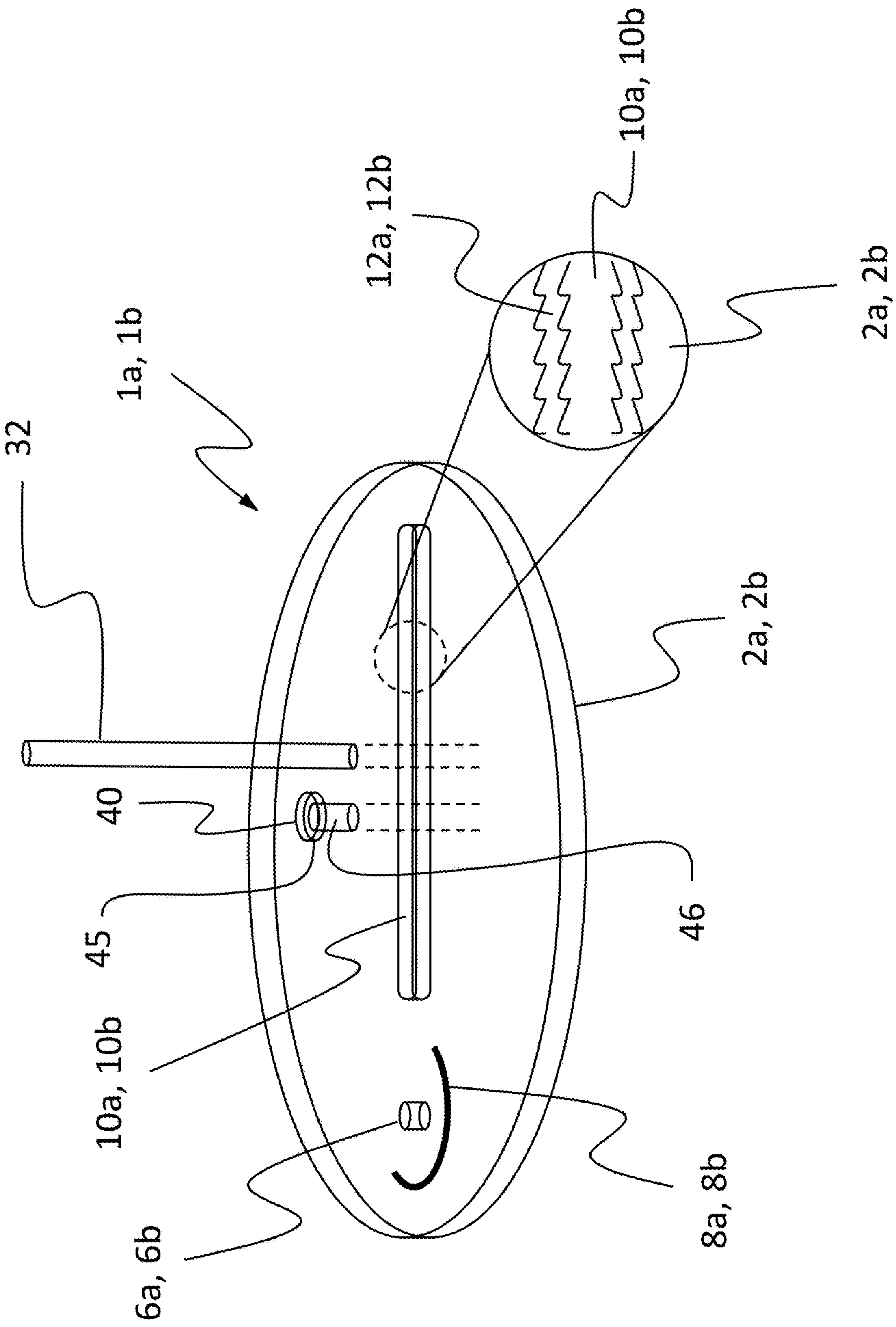
FIG. 12 is a schematic perspective view of a part of a third embodiment of a kit comprising two external fixators, a plurality of Kirschner wires and a stopper.

In order to prevent the second one 32 of the Kirschner wires from sliding back along the main slots 10*a*, 10*b* in a direction towards the through holes 6*a*, 6*b*, the kit may further comprise one or more stoppers 40 adapted to engage with the dentilated inner surfaces 12*a*, 12*b* of the main slots 10*a*, 10*b*, as shown in FIG. 12. FIG. 12 schematically shows part of a third embodiment of a kit, which comprises such a stopper 40, as well as a congruent pair of external fixators 1*a*, 1*b* and a plurality of Kirschner wires. The fit of each stopper 40 with one of the main slots 10*a*, 10*b* may be a friction fit or a click-fit, for example. Each stopper 40 may be made of a stiff plastics material manufactured by injection moulding, for example. The plastics material may comprise an antimicrobial additive, such as a silver compound.

Each stopper 40 may have any convenient shape which engages with the dentilated inner surfaces 12*a*, 12*b* of the main slots 10*a*, 10*b*. For example, the stopper 40 may comprise a head 45 and a body 46. The head 45 enables a surgeon to manipulate the stopper 40 and to insert it into one of the main slots 10*a*, 10*b*. The body 46 has a maximum width such that it fits between an adjacent pair of dentilations on the inner surfaces 12*a*, 12*b* of the main slots 10*a*, 10*b*, but cannot slide along the main slots 10*a*, 10*b* from between one adjacent pair of dentilations to between the next adjacent pair of dentilations. FIG. 12 shows the stopper 40 inserted into one of the main slots 10*a*, 10*b*, abutting the second one 32 of the Kirschner wires and on a side of the Kirschner wire 32 which is nearer to the through hole 6 than the Kirschner wire 32. Thus the Kirschner wire 32 is prevented by the stopper 40 from sliding along the main slots 10*a*, 10*b* in a direction towards the through holes 6*a*, 6*b*.

Figure 13:
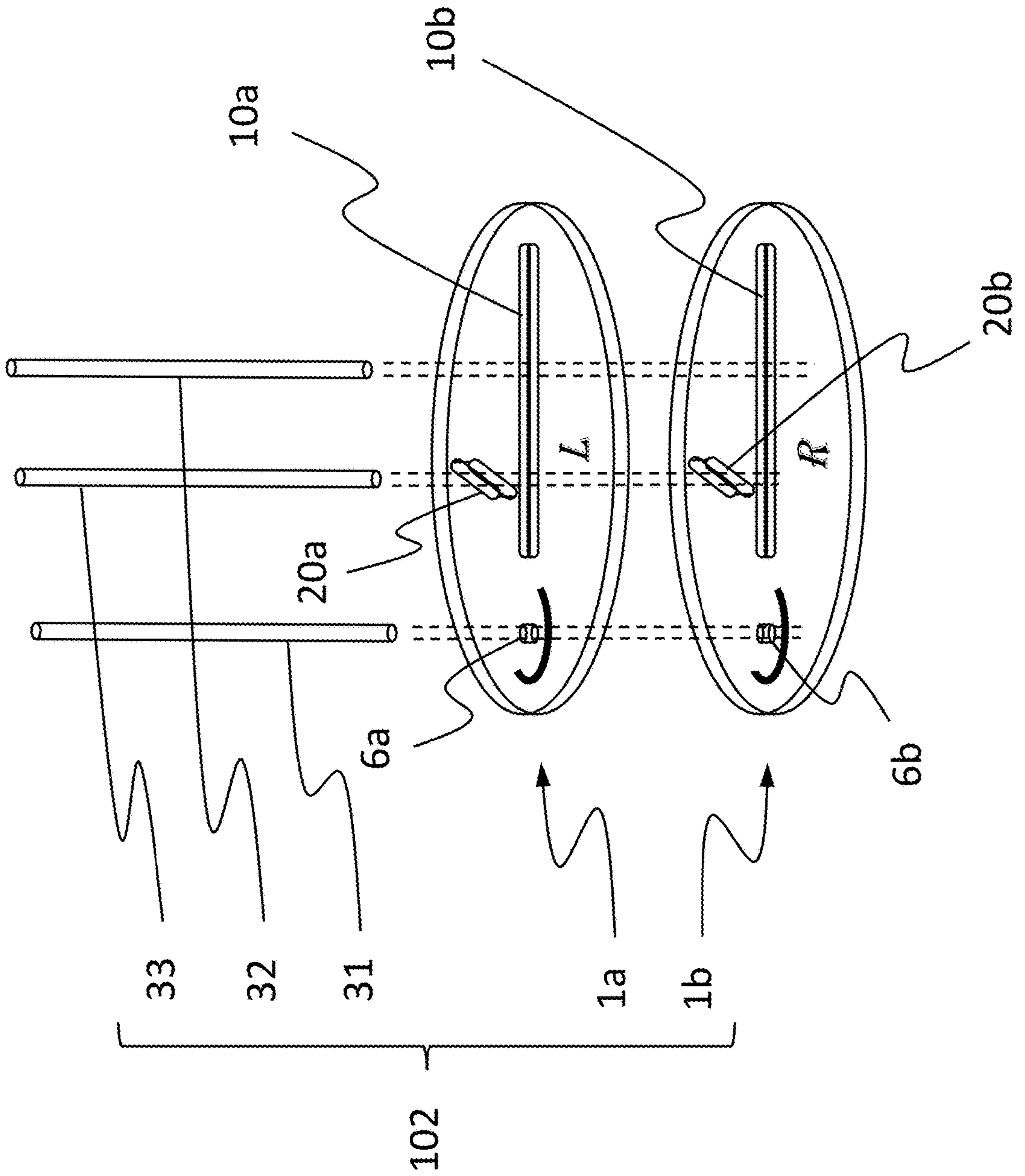
FIG. 13 is a schematic perspective view of a fourth embodiment of a kit comprising two external fixators and a plurality of Kirschner wires.

FIG. 13 schematically shows a fourth embodiment of a kit 102 comprising a congruent pair of external fixators 1*a*, 1*b* and three Kirschner wires 31, 32, 33. The pair of external fixators 1*a*, 1*b* are the same as those shown in the embodiment of FIG. 11, except that each external fixator 1*a*, 1*b* further comprises a respective subsidiary slot 20*a*, 20*b*, which connects the parallel opposite sides of the planar members 2*a*, 2*b* with each other, in the manner of the slot 20 of the external fixator 1 shown and described above in relation to FIG. 3. A first one 31 of the Kirschner wires has a diameter which fits through the through hole 6*a*, 6*b* in each of the pair of external fixators 1*a*, 1*b*. A second one 32 of the Kirschner wires has a diameter which fits through the main slot 10*a*, 10*b* in each of the pair of external fixators 1*a*, 1*b*, but is restrained by the dentilated inner surfaces 12*a*, 12*b* of the main slots 10*a*, 10*b* from sliding freely along the main slots 10*a*, 10*b*, in the manner described above in relation to FIG. 1. A third one 33 of the Kirschner wires has a diameter which fits through the subsidiary slot 20*a*, 20*b* in each of the pair of external fixators 1*a*, 1*b*, but is restrained by the dentilated inner surfaces 22*a*, 22*b* of the subsidiary slots 20*a*, 20*b* from sliding freely along the subsidiary slots 20*a*, 20*b*. If the width of the subsidiary slots 20*a*, 20*b* is the same as the width of the main slots 10*a*, 10*b* and as the diameter of the through holes 6*a*, 6*b*, the diameter of the third Kirschner wire 33 may be the same as the diameter of the first and second Kirschner wires 31, 32.

In use, a patient's finger is interposed between the congruent pair of external fixators 1*a*, 1*b* and the first and second Kirschner wires 31, 32 are inserted as described above in relation to FIG. 11. The third Kirschner wire 33 is inserted through the subsidiary slot 20*a* in the first one 1*a* of the pair of external fixators, through, over or under the middle phalanx P2 of the patient's finger (or if P2 is fragmented, through, over or under a fragment of P2) and through the subsidiary slot 20*b* in the second one 1*b* of the pair of external fixators. In order to reduce subluxation of the middle phalanx P2 (or a fragment thereof), the third Kirschner wire 33 is moved along the subsidiary slots 20*a*, 20*b* in a direction towards the through holes 6*a*, 6*b*.

Figure 14:
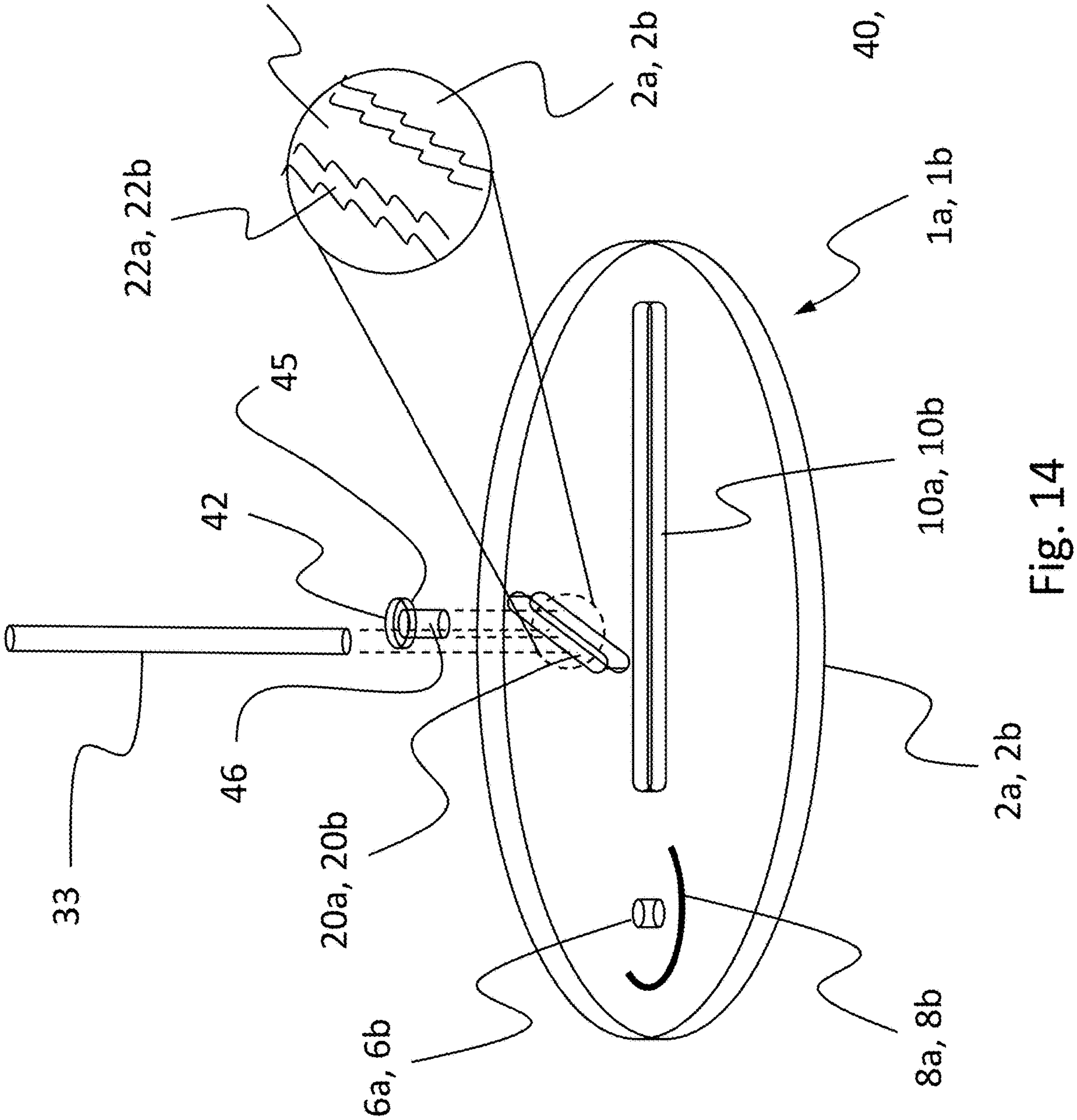
FIG. 14 is a schematic perspective view of a part of a fifth embodiment of a kit comprising two external fixators, a plurality of Kirschner wires and a stopper.

In order to prevent the third one 33 of the Kirschner wires from sliding back along the subsidiary slots 20*a*, 20*b*, the kit may further comprise one or more stoppers 42 adapted to engage with the dentilated inner surfaces 22*a*, 22*b* of the subsidiary slots 20*a*, 20*b*, as shown in FIG. 14. FIG. 14 schematically shows part of a fifth embodiment of a kit, which comprises such a stopper 42, as well as a congruent pair of external fixators 1*a*, 1*b* and a plurality of Kirschner wires, including the third one 33 of the Kirschner wires. The fit of each stopper 42 with one of the subsidiary slots 20*a*, 20*b* may be a friction fit or a click-fit, for example. Each stopper 42 may be made of a stiff plastics material manufactured by injection moulding, for example. The plastics material may comprise an antimicrobial additive, such as a silver compound.

Each stopper 42 may have any convenient shape which engages with the dentilated inner surfaces 22*a*, 22*b* of the subsidiary slots 20*a*, 20*b*. For example, the stopper 42 may comprise a head 45 and a body 46 in a similar manner to the stopper 40 described above in relation to FIG. 11. The head 45 of the stopper 42 enables a surgeon to manipulate the stopper 42 and to insert it into one of the subsidiary slots 20*a*, 20*b*. The body 46 has a maximum width such that it fits between an adjacent pair of dentilations on the inner surfaces 22*a*, 22*b* of the subsidiary slots 20*a*, 20*b*, but cannot slide along the subsidiary slots 20*a*, 20*b* from between one adjacent pair of dentilations to between the next adjacent pair of dentilations.

The stopper 42 may be inserted into one of the subsidiary slots 20*a*, 20*b* on either side of the Kirschner wire 33, depending on which direction along the one of the subsidiary slots 20*a*, 20*b* movement of the Kirschner wire 33 is to be prevented. FIG. 13 shows an example in which the stopper 42 is inserted into one of the subsidiary slots 20*a*, 20*b*, abutting the third one 33 of the Kirschner wires and on a side of the Kirschner wire 33 which is further from the through hole 6 than the Kirschner wire 33. Thus the Kirschner wire 33 is prevented by the stopper 42 from sliding along the subsidiary slots 20*a*, 20*b* in a direction away from the through holes 6*a*, 6*b*.

Figure 14A:
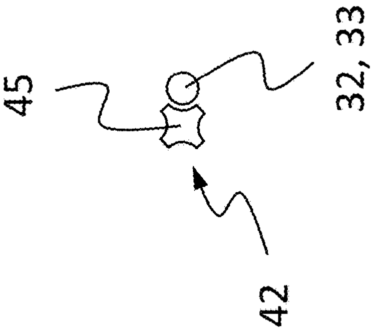
FIG. 14A is a schematic top plan view of an embodiment of a stopper abutting a Kirschner wire.

Advantageously, the head 45 of either of the stoppers 40, 42 shown and described above in relation to FIGS. 12 and 14 may have a shape which is complementary to the circular cross-section of a cylindrical Kirschner wire 32, 33. Whereas the stoppers 40, 42 shown in FIGS. 12 and 14 both have a disc-shaped head 45, which therefore has a circular cross-section, such a cross-section only engages with a cylindrical Kirschner wire tangentially. In contrast, FIG. 14A schematically shows a top plan view of an alternative embodiment of a stopper 40, 42 comprising a head 45 which has a cruciform shape, wherein the arms of the cross-shaped head 45 are joined to each other by circular arcs. Each of these circular arcs has a radius which is similar to, but slightly larger than, the radius of a Kirschner wire 32, 33 which the stopper 40, 42 is designed to be used with. Thus if the stopper 40, 42 of FIG. 14A is placed abutting a Kirschner wire 32, 33, one of these circular arcs contacts the Kirschner wire 32, 33 in the manner shown in FIG. 14A.

Figure 15:
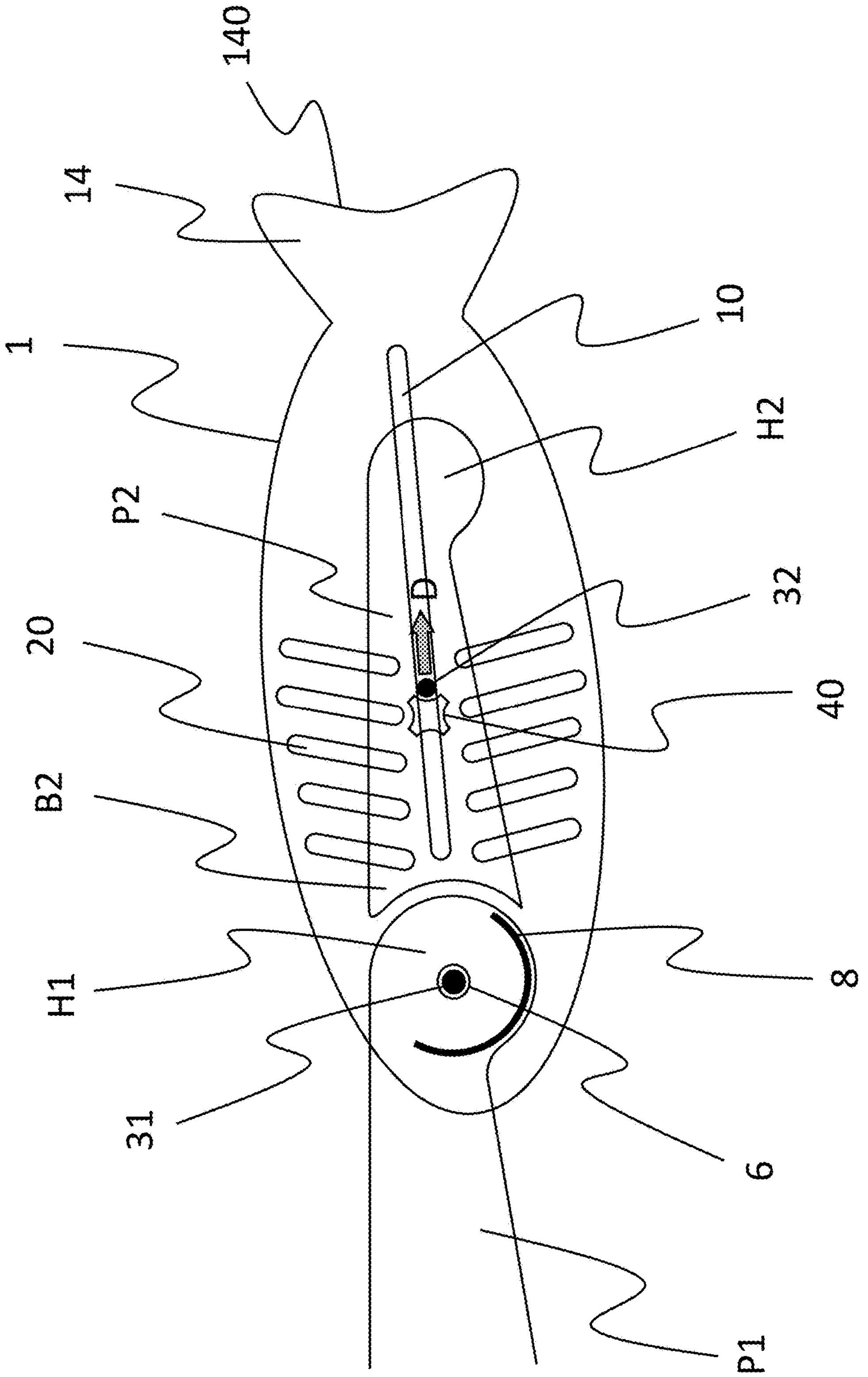
FIG. 15 is a schematic side elevational view of an ninth embodiment of an external fixator in situ on a PIP joint.

FIG. 15 schematically shows a ninth embodiment of an external fixator 1 in situ on a proximal interphalangeal (PIP) joint. The PIP joint comprises a proximal phalanx P1 and a middle phalanx P2. The PIP joint is formed by the condyle or head H1 of the proximal phalanx P1 and the base B2 of the middle phalanx P2. The external fixator 1 comprises a circular through hole 6, a semicircular arc 8 of radio-opaque material, a main slot 10, a tail 14, and a plurality of subsidiary slots 20. To fix the external fixator 1 to the PIP joint, the arc 8 is carefully aligned with an outline of the head H1 of the proximal phalanx P1 using X-ray imaging, until the through hole 6 is centred on the head H1. A first Kirschner wire 31 is then inserted through the through hole 6 and the centre of the head H1 of the proximal phalanx P1. A second Kirschner wire 32 is then inserted through the main slot 10 and the middle phalanx P2 at a convenient location. In order to apply distraction to the PIP joint, the second Kirschner wire 32 is then moved along the main slot 10 in the direction of the arrow D, whilst pressing on surface 140 of tail 14 in the opposite direction to arrow D, to hold the fixator 1 in position as the second Kirschner wire 32 moves relative to the fixator 1. Finally, a stopper 40 is inserted into the main slot 10, abutting the second Kirschner wire 32 on the side of the second Kirschner wire 32 which is nearer to the through hole 6, to prevent the second Kirschner wire 32 from sliding back along the main slot 10 towards the through hole 6, which would otherwise reduce the applied distraction.

Whereas FIG. 15 shows only a single external fixator 1, a second, congruent external fixator is also located on the opposite side of the PIP joint from the external fixator 1 shown in FIG. 15. Thus the first and second Kirschner wires 31, 32 exit the proximal and middle phalanges P1, P2, respectively, and pass through the through hole 6 and the main slot 10, respectively, of the second, congruent external fixator. A second stopper 40 is then also inserted into the main slot 10 of the second, congruent external fixator in a location opposite that of the stopper 40 shown in FIG. 15 to prevent the second Kirschner wire 32 from sliding along the main slot 10 of the second, congruent external fixator as well.

Figure 16:
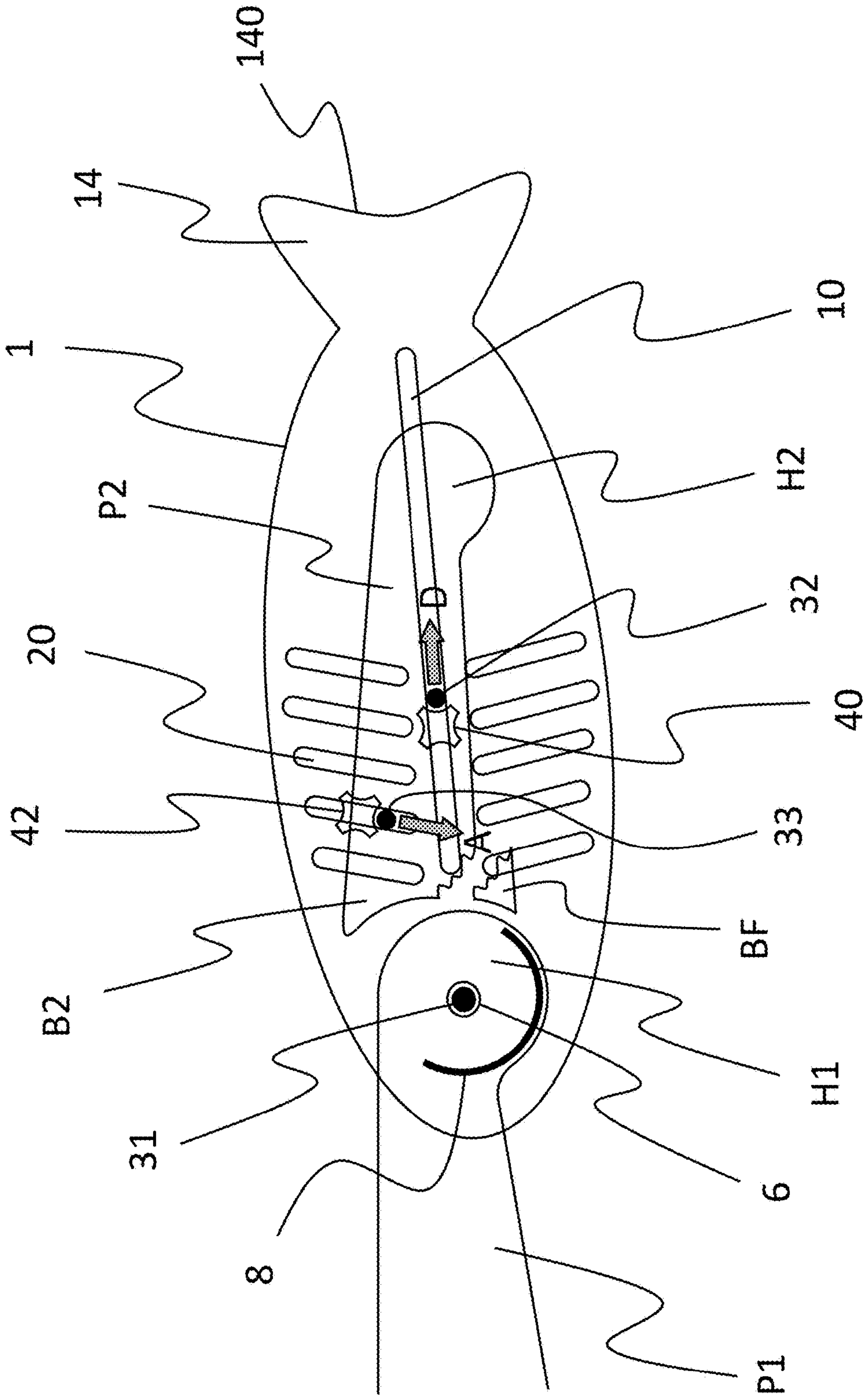
FIG. 16 is a schematic side elevational view of the ninth embodiment of an external fixator shown in FIG. 15 in situ on another PIP joint.

FIG. 16 schematically shows the external fixator 1 of FIG. 15 in situ on another PIP joint. In this case, the middle phalanx P2 is broken, resulting in a bone fragment BF and dorsal subluxation of the middle phalanx P2. To fix the external fixator 1 to this PIP joint, the same steps as described above in relation to FIG. 15 are firstly carried out. A third Kirschner wire 33 is then inserted through a conveniently located one of the plurality of subsidiary slots 20 and the middle phalanx P2. The third Kirschner wire 33 is then moved along the chosen subsidiary slot 20 in the direction of the arrow A, in order to reduce the subluxation of the middle phalanx P2. Finally, a stopper 42 is inserted into the same subsidiary slot 20, abutting the third Kirschner wire 33 on the side of the third Kirschner wire 33 which is further from the through hole 6, to prevent the third Kirschner wire 33 from sliding along this subsidiary slot 20 away from the through hole 6, which would otherwise increase the dorsal subluxation of the middle phalanx P2 again.

As in FIG. 15, the second, congruent external fixator located on the opposite side of the PIP joint is not shown in FIG. 16 either. However, when the third Kirschner wire 33 exits the middle phalanx P2, it passes through the corresponding one of the subsidiary slots of the second, congruent external fixator. A second stopper 42 is then also inserted into this subsidiary slot of the second, congruent external fixator in a location opposite that of the stopper 42 shown in FIG. 15, to prevent the third Kirschner wire 33 from sliding along this subsidiary slot of the second, congruent external fixator as well.

Figure 17A:
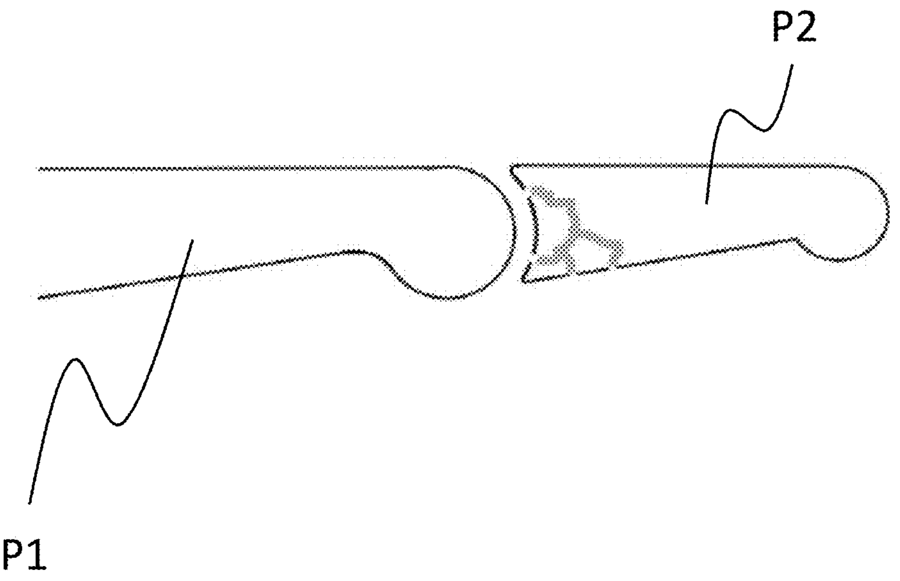
FIG. 17A is a schematic side elevational view of a fractured PIP joint.
Figure 17B:
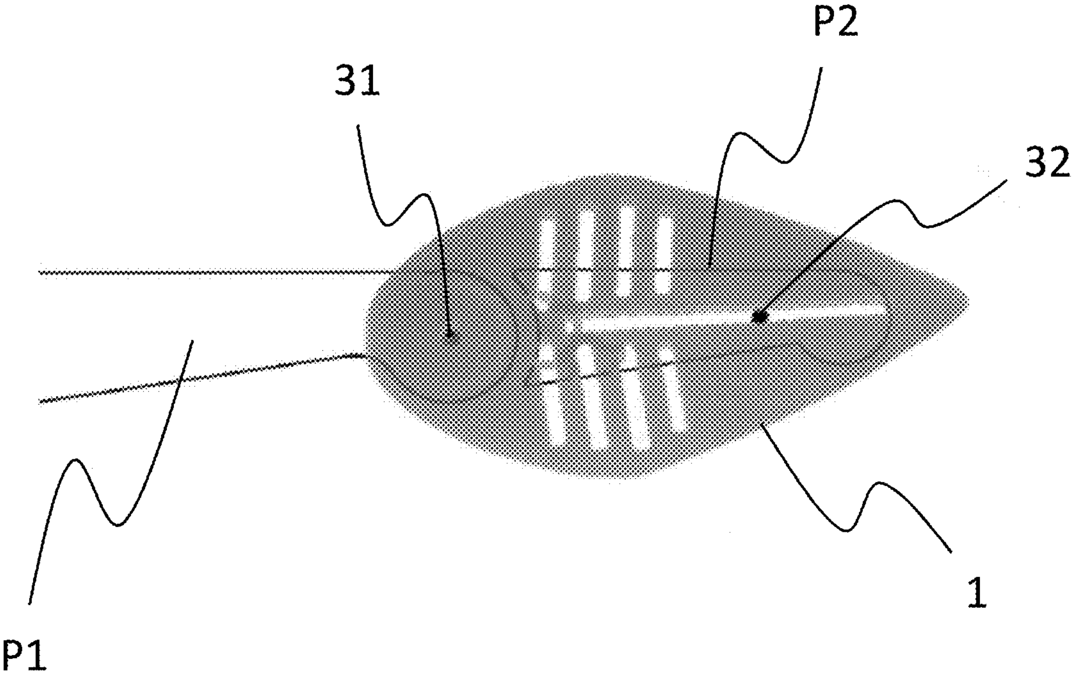
FIG. 17B is a schematic side elevational view of an embodiment of an external fixator and a plurality of Kirschner wires applied to the PIP joint shown in FIG. 17A.

FIG. 17A schematically shows a fractured PIP joint, in which the middle phalanx P2 exhibits multiple fractures, but in which the fragments of the middle phalanx P2 remain unseparated from each other. FIG. 17B schematically shows an embodiment of an external fixator 1 and two Kirschner wires 31, 32 fixed to the PIP joint of FIG. 17A, to apply a distraction force to the PIP joint. The external fixator 1 is fixed to the PIP joint using the same technique as was described above in relation to FIG. 15.

Figure 18A:
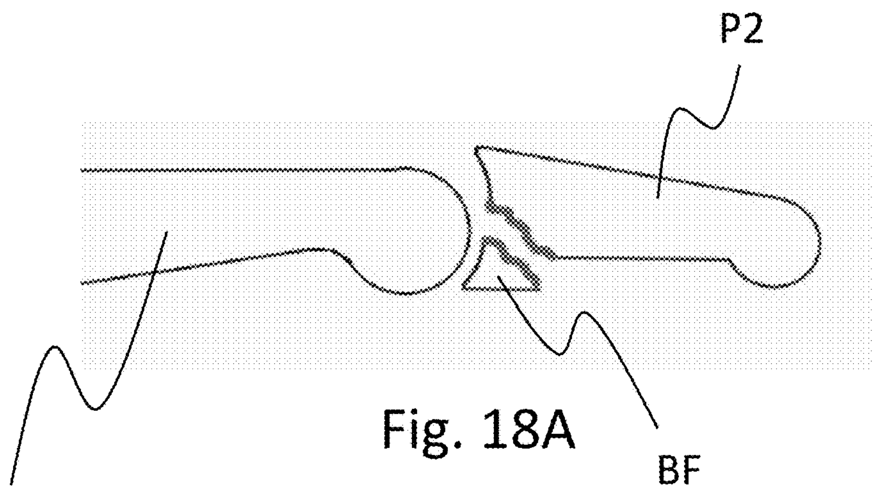
FIG. 18A is a schematic side elevational view of another fractured PIP joint.
Figure 18B:
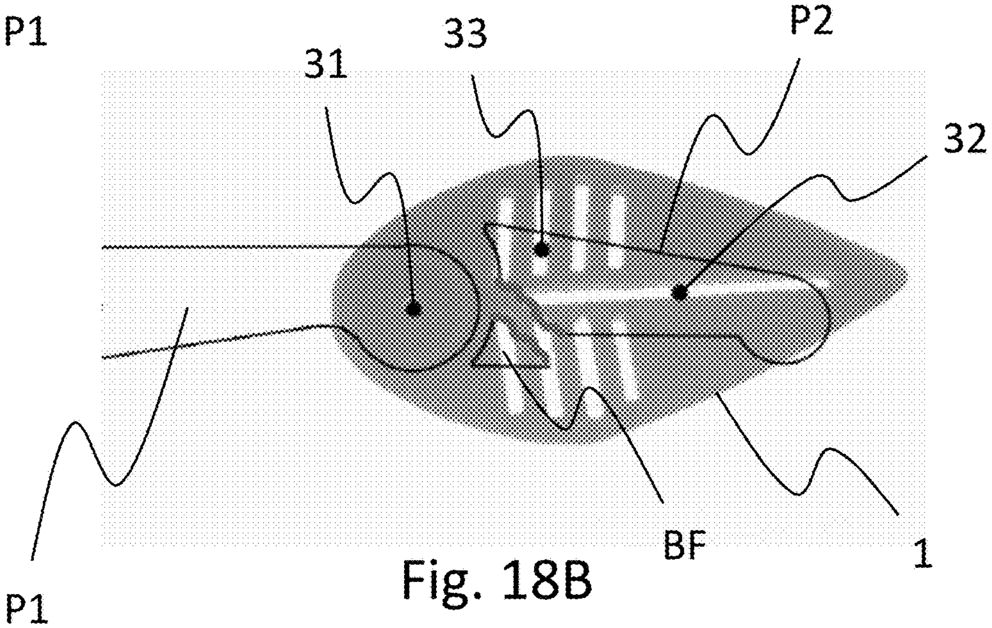
FIGS. 18B and 18C are schematic side elevational views of successive stages in application of an embodiment of an external fixator and a plurality of Kirschner wires to the PIP joint shown in FIG. 18A.
Figure 18C:
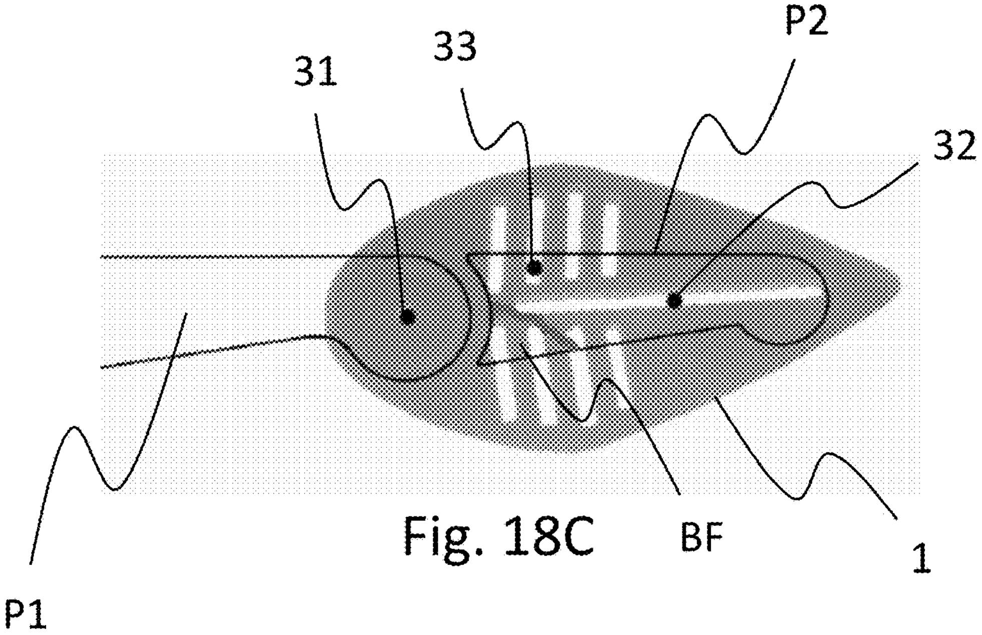

FIG. 18A schematically shows another fractured PIP joint, in which the middle phalanx P2 is broken, resulting in a bone fragment BF and dorsal subluxation of the middle phalanx P2. FIGS. 18B and 18C schematically show successive stages in fixation of the same embodiment of an external fixator 1 as shown in FIG. 17B and three Kirschner wires 31, 32, 33 to the PIP joint of FIG. 18A, in order to apply a distraction force to the PIP joint and to reduce the dorsal subluxation of the middle phalanx P2. The external fixator 1 is fixed to the PIP joint using the same technique as described above in relation to FIG. 16.

FIG. 18B shows a condition of the external fixator 1 after the third Kirschner wire 33 has been inserted through a conveniently located one of the plurality of subsidiary slots in the external fixator 1 and the middle phalanx P2, but before it has been moved along the chosen subsidiary slot. FIG. 18C shows a condition of the external fixator 1 after the third Kirschner wire 33 has been moved along this subsidiary slot in a direction towards the main slot, in order to reduce the subluxation of the middle phalanx P2, thereby bringing the middle phalanx P2 back into alignment with the proximal phalanx P1 and back into contact with the bone fragment BF. The third Kirschner wire 33 may then be held in place by a suitably located stopper inserted into the subsidiary slot in the manner described above in relation to FIG. 16.

Figure 19A:
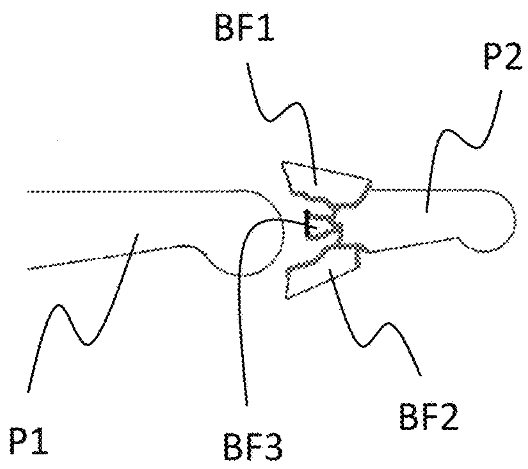
FIG. 19A is a schematic side elevational view of a PIP joint exhibiting a pilon fracture.
Figure 19C:
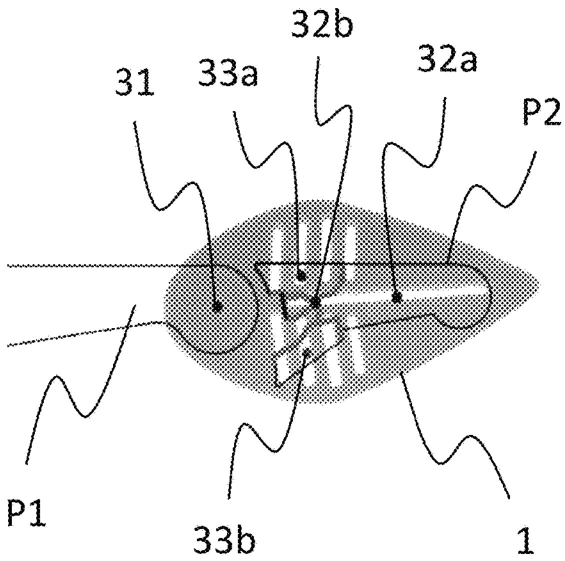
FIGS. 19B to 19D are schematic side elevational views of successive stages in application of an embodiment of an external fixator and a plurality of Kirschner wires to the PIP joint shown in FIG. 18A.
Figure 19B:
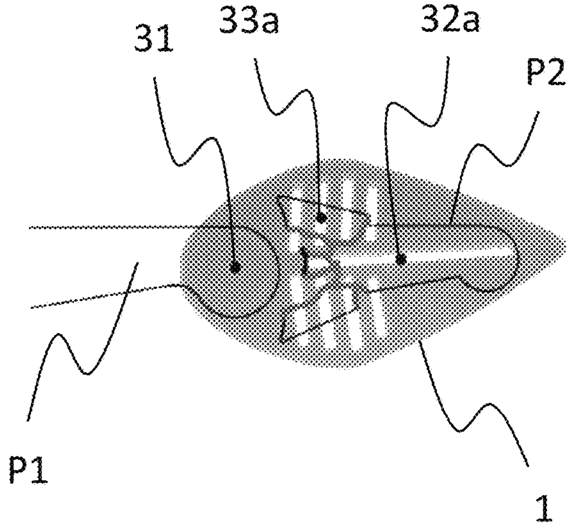
Figure 19D:
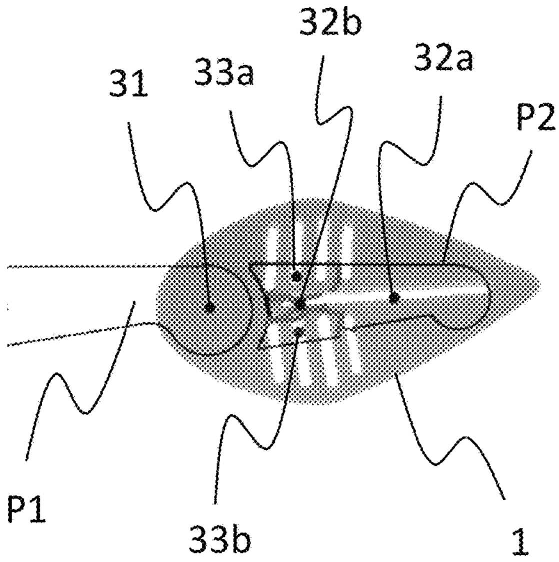

FIG. 19A schematically shows a PIP joint exhibiting a pilon fracture, in which the middle phalanx P2 is broken, resulting in a plurality of bone fragments. A first one BF1 of these bone fragments exhibits dorsal subluxation and a second one BF2 of these bone fragments exhibits volar subluxation. A third one BF3 of these bone fragments is impacted distally into the middle phalanx P2. FIGS. 19B to 19D schematically show successive stages in fixation of the same embodiment of an external fixator 1 as shown in FIG. 17B and a plurality of Kirschner wires to the PIP joint of FIG. 19A, in order to correct this pilon fracture.

Firstly, in FIG. 19B, a first Kirschner wire 31 is inserted through the through hole of the external fixator 1 and the condyle or head of the proximal phalanx P1 in the manner described above in relation to FIG. 15. A second Kirschner wire 32*a* is then inserted through the main slot in the external fixator 1 and the middle phalanx P2, and a third Kirschner wire 33*a* is inserted through a conveniently located one of the subsidiary slots in the external fixator 1 and the bone fragment BF1.

FIG. 19C shows a condition of the external fixator 1 after the third Kirschner wire 33*a* has been moved along this subsidiary slot in a direction towards the main slot, in order to reduce the dorsal subluxation of the bone fragment BF1. FIG. 19C also shows that a fourth Kirschner wire 32*b* has been inserted through the main slot in the external fixator 1 and between the impacted bone fragment BF3 and the middle phalanx P2. In addition, a fifth Kirschner wire 33*b* has been inserted through another conveniently located one of the subsidiary slots in the external fixator 1 and the bone fragment BF2.

FIG. 19D shows a condition of the external fixator 1 after the fifth Kirschner wire 33*b* has been moved along this subsidiary slot in a direction towards the main slot, in order to reduce the volar subluxation of the bone fragment BF2. In addition, the fourth Kirschner wire 32*b* has also been moved along the main slot in a direction towards the through hole in the external fixator 1, whilst the second Kirschner wire 32*a* holds the middle phalanx P2 in place relative to the proximal phalanx P1. This movement of the fourth Kirschner wire 32*b* pushes the bone fragment BF3 towards the head of the proximal phalanx P1 and brings the bone fragment BF3 back into alignment with the bone fragments BF1 and BF2. All of the Kirschner wires may then be held in place by suitably located stoppers inserted into the main and subsidiary slots in the manner described above in relation to FIGS. 15 and 16.

FIGS. 19A to 19D demonstrate that more than one Kirschner wire may be inserted through any one of the main and subsidiary slots in an embodiment of an external fixator according to the present invention, in order to correct complex fractures of a PIP joint.

Figure 20:
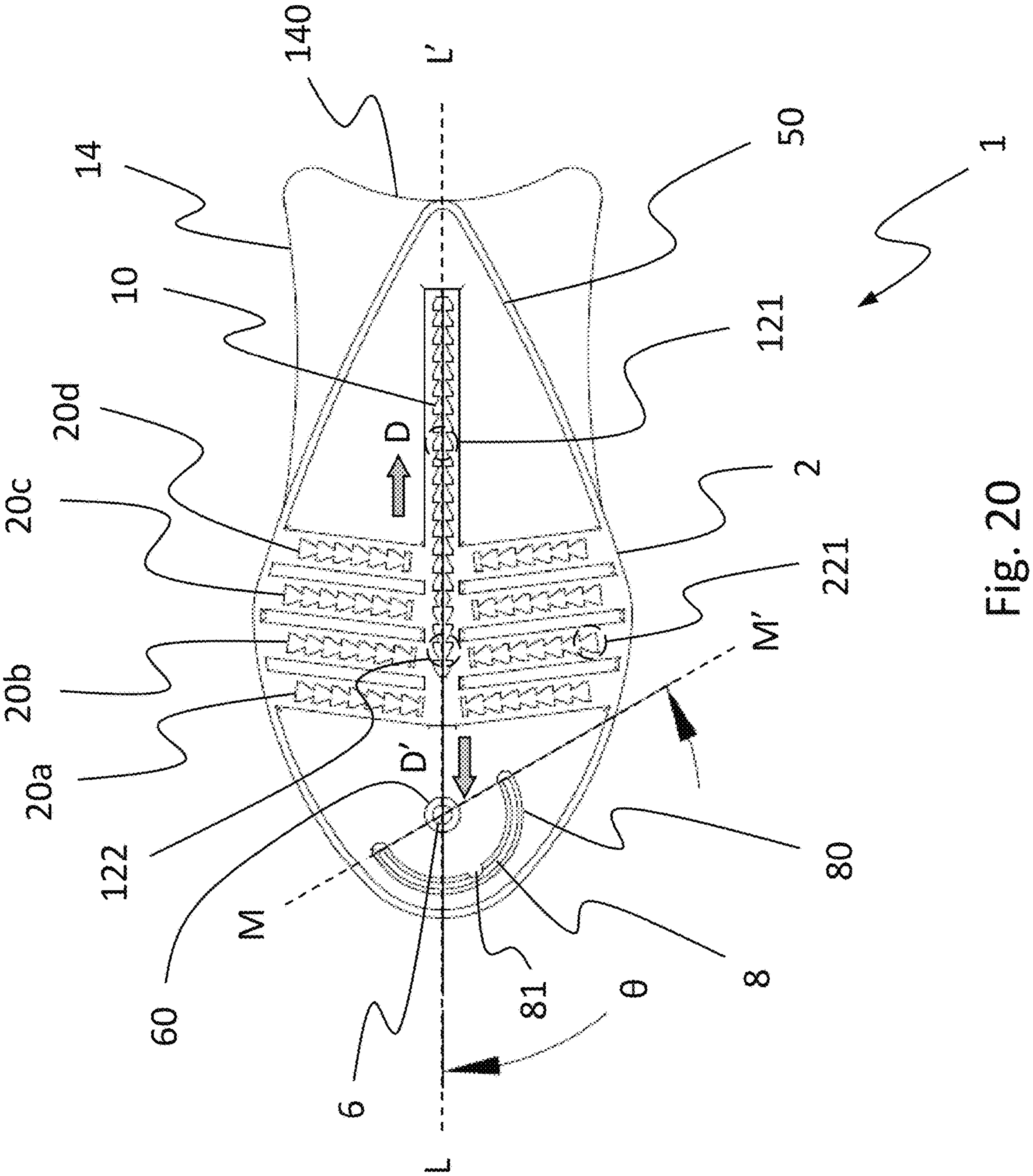
FIG. 20 is a schematic top plan view of a tenth embodiment of an external fixator.

FIG. 20 schematically shows a tenth embodiment of an external fixator 1. The external fixator 1 of FIG. 20 has a similar form to that shown in FIGS. 17B, 18B to 18C and 19B to 19D, but differs therefrom in several respects, as follows.

Firstly, the external fixator 1 of FIG. 20 further comprises a tail 14. The tail 14, which is bifurcate, is arranged symmetrically about the longitudinal axis L-L' of the planar member 2 of the fixator 1 and comprises a concave surface 140 at an opposite end of the planar member 2 from the through hole 6. The tail 14 allows for manipulation of the fixator 1, by providing a handle, for example to attach an instrument such as an artery clip or haemostat, as described previously, whereby the fixator 1 may be held. The concave surface 140 provides a point of purchase on which a surgeon may apply a force to the fixator 1 in the direction indicated in FIG. 20 by the arrow labelled D'.

Secondly, the external fixator 1 of FIG. 20 also differs from the external fixator 1 shown in FIGS. 17B, 18B to 18C and 19B to 19D in that in this case, the arc 8 of radio-opaque material which is centred on the through hole 6, instead of being embedded within and enclosed by the planar member 2, comprises a stainless-steel insert, which for ease of manufacture, is clipped into a groove 80 formed in a surface of the planar member 2. The stainless-steel insert of arc 8 is held in place within the groove 80 by a lip 81, which overhangs the groove 80. Each end of the arc 8 defines a line M-M', which subtends an angle θ with the longitudinal axis L-L' of the planar member 2. In this embodiment, the angle θ is approximately equal to 120 degrees.

Furthermore, in order to improve the strength and rigidity of the external fixator 1, the planar member 2 is surrounded by a perimeter wall 50 of greater thickness than the rest of the planar member 2. For the same reason, the wall 50 also extends around the main slot 10 and around each of the subsidiary slots 20*a*, 20*b*, 20*c* and 20*d*. The through hole 6 is similarly surrounded by a circular wall 60. For example, the planar member 2 may have a thickness of about 2 to 3 mm, whereas the walls 50, 60 may each have a thickness of about 4 mm.

As may also be seen in FIG. 20, the dentilated inner surface of the main slot 10 comprises a first plurality of dentilations 121, each of which tapers in a direction along the main slot 10 which is away from the through hole 6. In addition, the dentilated inner surface of each of the subsidiary slots 20*a*, 20*b*, 20*c* and 20*d* each comprises a second respective plurality of dentilations 221, each of which tapers in a direction along the respective subsidiary slot 20*a*, 20*b*, 20*c*, 20*d* towards the main slot 10. Finally, the dentilated inner surface of the main slot 10 further comprises a third plurality of dentilations 122, which are located closer to the through hole 6 than the first plurality of dentilations 121 and each taper in a direction along the main slot 10 which is towards the through hole 6, and therefore opposite to the direction in which the first plurality of dentilations 121 taper.

The first plurality of dentilations 121 allows a Kirschner wire to be ratcheted in the direction indicated in FIG. 20 by the arrow labelled D, as follows. If the Kirschner wire has a diameter which is less than the widest part of the dentilations 121 but more than the narrowest part of the dentilations 121, it will induce a slight flexure of the rigid planar member 2 if the wire is moved from one of the dentilations 121 to the next adjacent dentilation, thereby easing the dentilated inner surfaces of the main slot 10 slightly apart from each other and temporarily increasing the width of the main slot 10 by a small amount, through elastic deformation of the planar member 2. Thus the Kirschner wire can be pushed against a force applied to the concave surface 140 of the tail 14, which force is applied in the direction indicated in FIG. 20 by the arrow labelled D' and opposite to the direction of movement of the Kirschner wire. Such a movement of the Kirschner wire is therefore similar to that described above in relation to the Kirschner wire 32*a* shown in FIGS. 19B to 19D.

On the other hand, the third plurality of dentilations 122 in the main slot 10 allows a Kirschner wire to be ratcheted in the opposite direction, as indicated in FIG. 20 by the arrow labelled D', as follows. If, once again, the Kirschner wire has a diameter which is less than the widest part of the dentilations 122 but more than the narrowest part of the dentilations 122, it will also induce a slight flexure of the rigid planar member 2 if the wire is moved from one of the dentilations 122 to the next adjacent dentilation. Thus such a Kirschner wire can be pushed in the direction indicated in FIG. 20 by the arrow labelled D', for example in order to realign a bone fragment in a pilon fracture such as the bone fragment BF3 shown in FIG. 19A. Movement of the Kirschner wire in this case is therefore similar to that described above in relation to the Kirschner wire 32*b* shown in FIGS. 19B to 19D.

Finally, the second plurality of dentilations 221 formed in each respective one of the subsidiary slots 20*a*, 20*b*, 20*c* and 20*d* similarly allows a Kirschner wire to be ratcheted in a direction towards the main slot 10, by acting in the same manner to induce a slight flexure of the rigid planar member 2. Thus such a Kirschner wire can be pushed along a respective one of the subsidiary slots 20*a*, 20*b*, 20*c* and 20*d* towards the main slot 10, for example in order to realign a bone fragment in a pilon fracture such as the bone fragments BF1 and BF2 shown in FIG. 19A. Movement of such a Kirschner wire in this case is therefore similar to that described above in relation to the Kirschner wires 33*a* and 33*b* shown in FIGS. 19B to 19D.

Nonetheless, in the case of all the first, second and third pluralities of dentilations 121, 221, 122, it remains possible, by application of sufficient force in the right direction, to push against the prevailing direction of the dentilations, and therefore, for example, to relieve a distraction force which has already been applied to a joint, or to reposition a Kirschner wire at a different location within a respective one of the main slot 10 or the subsidiary slots 20*a*, 20*b*, 20*c*, 20*d*.

In general, an external fixator according to the present invention allows a wide variety of different joint fractures to be corrected by passing Kirschner wires through, over or under different anatomical components of the joint, and then using a congruent pair of external fixators of the invention to apply forces to these anatomical components in a controlled fashion. These forces may be applied by moving a Kirschner wire along the main, and possibly also subsidiary, slots of the external fixators in either direction of the respective slots. One or more Kirschner wires may also be inserted through the same slot according to the demands of the fractured joint which is subject to fixation and may be moved in the same or opposite directions from each other. There is also no limit on the number of Kirschner wires which may be used with an external fixator according to the invention, up to the maximum number of wires which can be accommodated within the slots of the fixator, which depends on the length of the slots.

Figure 21:
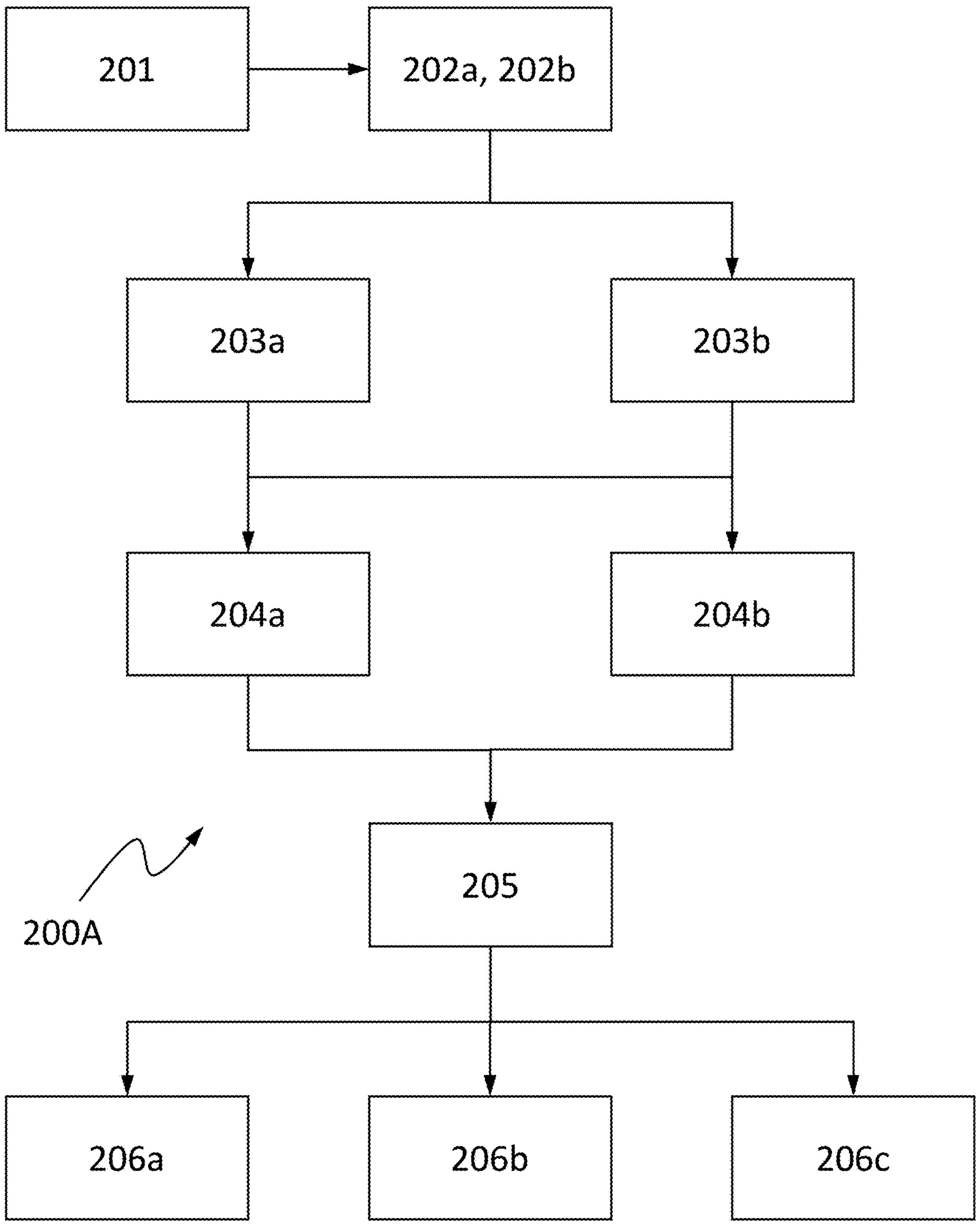
FIG. 21 is a schematic flow diagram of a first embodiment of a method which comprises providing a congruent pair of external fixators as described herein for use in a surgical operation.

FIG. 21 schematically shows a first embodiment 200A of a method of using a congruent pair of external fixators in a surgical operation. The method 200A comprises providing 201 a congruent pair of external fixators 1*a*, 1*b* of the type described above. In this embodiment, the rigid planar member 2*a*, 2*b* of each of the congruent pair of external fixators 1*a*, 1*b* is made of a radio-transparent material, and each of the congruent pair of external fixators 1*a*, 1*b* comprises a circular arc 8*a*, 8*b* of radio-opaque material centred on the through hole 6*a*, 6*b* of the respective one of the external fixators 1*a*, 1*b*. The through hole 6*a*, 6*b* of each of the congruent pair of external fixators 1*a*, 1*b* is aligned 202 with the centre of rotation of the condyle of a first bone proximal to a fracture complex, by aligning the arc 8*a*, 8*b* of radio-opaque material in each case with an outline of the condyle of the first bone, as they both appear on an X-ray image. The skin of the patient is then marked 202*b* through the through hole 6*a*, 6*b* of the respective one of the congruent pair of external fixators 1*a*, 1*b* with the centre of rotation of the condyle of the first bone.

These marks are then used as guides or targets to insert 203*a* a first Kirschner wire 31 having a diameter which fits through the through hole 6*a*, 6*b* in each of the pair of external fixators 1*a*, 1*b* transversely through the condyle of the first bone. A second Kirschner wire 32, 32*a* having a diameter which fits through the main slot 10*a*, 10*b* in each of the pair of external fixators 1*a*, 1*b*, but is restrained by the dentilated inner surfaces 12*a*, 12*b* of the main slots 10*a*, 10*b* from sliding freely along the main slots 10*a*, 10*b*, is also inserted 203*b* transversely through a second bone distal to the fracture complex and parallel to the first Kirschner wire 31. The first and second Kirschner wires 31, 32, 32*a* may be thus inserted in either order.

Next, a first one 1*a* of the congruent pair of external fixators is threaded 204*a* over the first 31 and second 32, 32*a* Kirschner wires on a first lateral side of the fracture complex, by passing the first Kirschner wire 31 through the circular through hole 6*a* and the second Kirschner wire 32, 32*a* through the main slot 10*a* of the first external fixator 1*a*. The second one 1*b* of the congruent pair of external fixators is also threaded 204*b* over the first 31 and second 32, 32*a* Kirschner wires on a second, opposing lateral side of the fracture complex in a similar fashion, by passing the first Kirschner wire 31 through the circular through hole 6*b* and the second Kirschner wire 32, 32*a* through the main slot 10*b* of the second external fixator 1*b*. Once again, the first and second ones of the congruent pair of external fixators 1*a*, 1*b* may be thus threaded over the first and second Kirschner wires 31, 32, 32*a* in either order.

A distraction force is then applied 205 to the fracture complex by increasing the separation between the first 31 and second 32, 32*a* Kirschner wires, by moving the second Kirschner wire 32, 32*a* along the main slots 10*a*, 10*b* of each of the congruent pair of external fixators 1*a*, 1*b* in a direction away from the through hole 6*a*, 6*b* of each respective one of the congruent pair of external fixators 1*a*, 1*b*. Finally, the second Kirschner wire 32, 32*a* is locked in place on each of the congruent pair of external fixators 1*a*, 1*b* by at least one of the following techniques. Inserting 206*a* a stopper of a type described above into the main slot 10*a*, 10*b* on the side of the second Kirschner wire 32, 32*a* which is nearer to the through hole 6*a*, 6*b* than the second Kirschner wire 32, 32*a*. Bonding 206*b* the second Kirschner wire 32, 32*a* to the rigid planar member 2*a*, 2*b*, for example with an adhesive. Inserting 206*c* a pin or screw which is thicker than a width of the main slot 10*a*, 10*b* into the main slot 10*a*, 10*b* on the side of the second Kirschner wire 32, 32*a* which is nearer to the through hole 6*a*, 6*b* than the second Kirschner wire 32, 32*a*.

Figure 22:
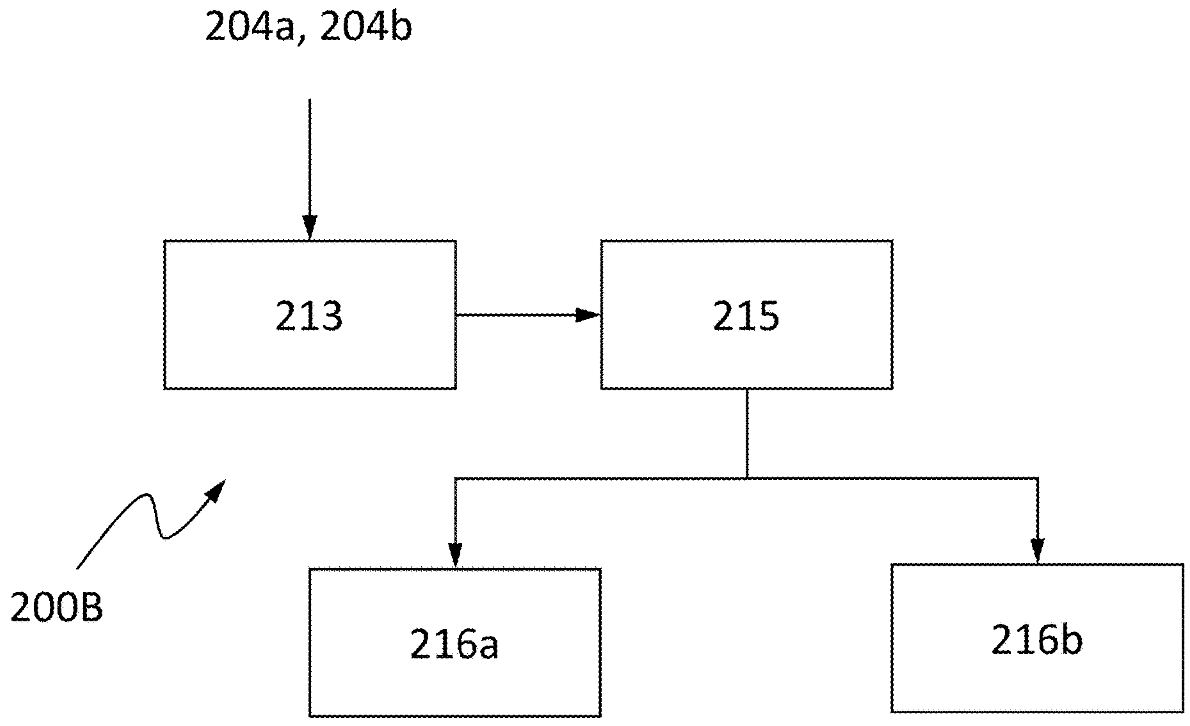
FIG. 22 is a schematic flow diagram of a second embodiment of such a method.

FIG. 22 schematically shows a second embodiment 200B of a method of using a congruent pair of external fixators in a surgical operation. The method 200B comprises at least the same procedures 201, 203*a*, 203*b*, 204*a*, 204*b*, 205, as well as at least one of 206*a*, 206*b*, 206*c*, as were described above in relation to FIG. 21. In this embodiment, however, the fracture complex comprises a bone fragment which is subject to subluxation. To address this situation, the rigid planar member 2*a*, 2*b* of each of the congruent pair of external fixators 1*a*, 1*b* which is provided 201 further comprises a subsidiary slot 20*a*, 20*b* connecting the parallel opposite sides 4*a*, 4*b* of the rigid planar member 2*a*, 2*b* with each other, wherein the subsidiary slot 20*a*, 20*b* extends away from the through hole 6*a*, 6*b*, oblique to the main slot 10*a*, 10*b* of each of the rigid planar members 2*a*, 2*b*, and has a dentilated inner surface 22*a*, 22*b*. The method therefore further comprises inserting 213 a third Kirschner wire 33, 33*a*, 33*b* having a diameter which fits through the subsidiary slot 20*a*, 20*b* in each of the pair of external fixators 1*a*, 1*b*, but is restrained by the dentilated inner surfaces 22*a*, 22*b* of the subsidiary slots 20*a*, 20*b* from sliding freely along the subsidiary slots 20*a*, 20*b*, transversely through the subsidiary slot 20*a*, 20*b* in each of the pair of external fixators 1*a*, 1*b* and through the bone fragment subject to subluxation, parallel to the first 31 and second 32, 32*a* Kirschner wires. Next, the subluxation of the bone fragment is reduced 215 by moving the third Kirschner wire 33, 33*a*, 33*b* in a direction towards the main slot 10*a*, 10*b* of each respective one of the congruent pair of external fixators 1*a*, 1*b*. The third Kirschner wire 33, 33*a*, 33*b* is then locked in place on each of the congruent pair of external fixators 1*a*, 1*b* by at least one of the following techniques. Inserting 216*a* a stopper of the type described above, or a pin or screw having a diameter which is greater than a width of the subsidiary slot 20*a*, 20*b* in each of the pair of external fixators, into the subsidiary slot 20*a*, 20*b* on the side of the third Kirschner wire 33, 33*a*, 33*b* which is further from the main slot 10*a*, 10*b* than the third Kirschner wire 33, 33*a*, 33*b*, and bonding 216*b* the third Kirschner wire 33, 33*a*, 33*b* to the rigid planar member 2*a*, 2*b*, for example using an adhesive.

Figure 23:
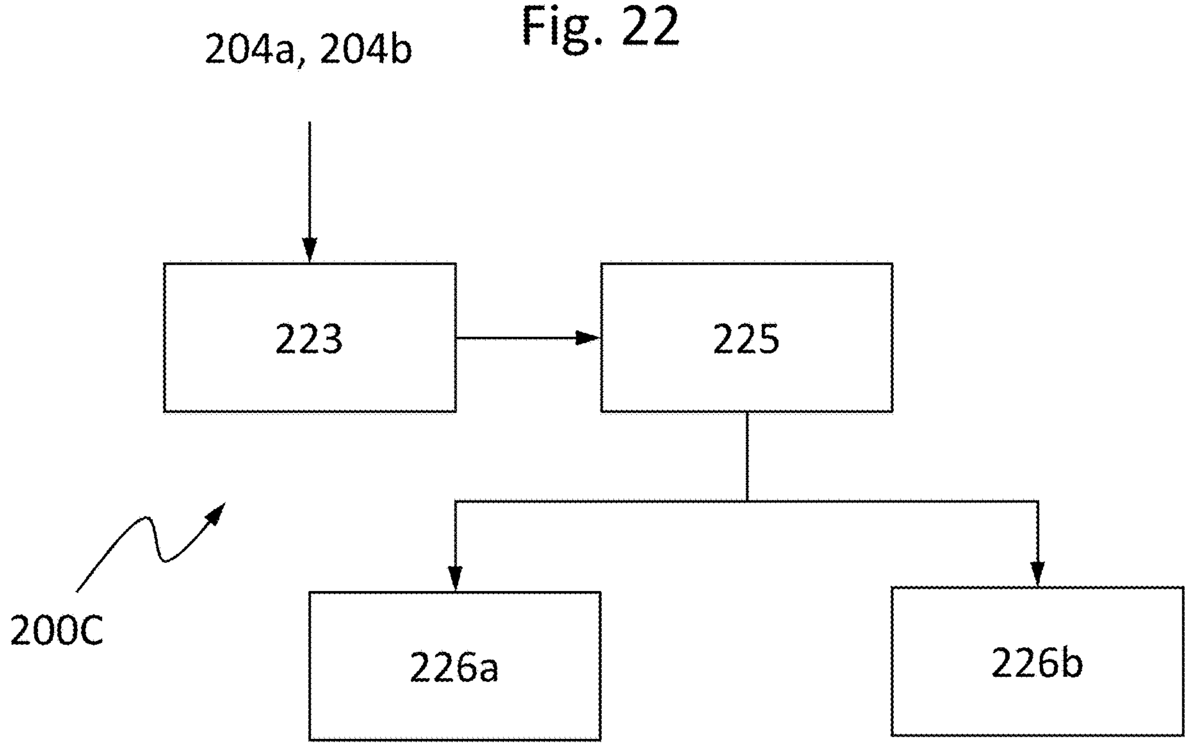
FIG. 23 is a schematic flow diagram of a third embodiment of such a method.

FIG. 23 schematically shows a third embodiment 200C of a method of using a congruent pair of external fixators in a surgical operation. The method 200C comprises at least the same procedures 201, 203*a*, 203*b*, 204*a*, 204*b*, 205, as well as at least one of 206*a*, 206*b*, 206*c*, as were described above in relation to FIG. 21, and may also be used in combination with the method 200B described above in relation to FIG. 22. In this embodiment, however, the fracture complex comprises a bone fragment which is impacted distally to the condyle of the first bone. To address this situation, the method therefore further comprises inserting 223 a fourth Kirschner wire 32*b* having a diameter which fits through the main slot 10*a*, 10*b* in each of the pair of external fixators 1*a*, 1*b*, but is restrained by the dentilated inner surfaces 12*a*, 12*b* of the main slots 10*a*, 10*b* from sliding freely along the main slots 10*a*, 10*b*, transversely through the main slot 10*a*, 10*b* in each of the pair of external fixators 1*a*, 1*b*, between the impacted bone fragment and the second bone, parallel to the first 31 and second 32, 32*a* Kirschner wires. The impaction of the bone fragment is then reduced by moving 225 the fourth Kirschner wire 32*b* along the main slots 10*a*, 10*b* of each of the congruent pair of external fixators 1*a*, 1*b* in a direction towards the through hole 6*a*, 6*b* of each respective one of the congruent pair of external fixators 1*a*, 1*b*. Finally, the fourth Kirschner wire 32*b* is locked in place on each of the congruent pair of external fixators 1*a*, 1*b* by at least one of the following techniques. Inserting 226*a* a stopper of the type described above, or a pin or screw having a diameter which is greater than a width of the main slot 10*a*, 10*b* in each of the pair of external fixators, into the main slot 10*a*, 10*b* on the side of the fourth Kirschner wire 32*b* which is further from the through hole 6*a*, 6*b* than the fourth Kirschner wire 32*b*, and bonding 226*b* the fourth Kirschner wire 32*b* to the rigid planar member 2*a*, 2*b*.

Whereas the present invention has been described above by reference to particular examples and embodiments, the scope of the invention should not be taken to be limited thereby and is instead defined by the appended claims. In particular, whereas the present invention has been described with particular reference to and using the example of fixation of a fractured PIP joint, an external fixator according to the invention, and a kit comprising the same, if suitably adapted in terms of shape and size, but still having the same features as defined by the claims, is equally applicable to fixation of other fractured joints, such as a DIP joint, as well as for use in ligamentotaxis more broadly.

The invention claimed is:

1. A kit comprising a congruent pair of external fixators for fixation of a fractured joint, wherein each of the pair of external fixators comprises a rigid planar member having a pair of parallel opposite sides, and wherein the planar member comprises:

a circular through hole normal to the parallel opposite sides; and a rectilinear main slot connecting the parallel opposite sides with each other;

wherein the main slot is radially aligned with the through hole, and has a dentilated inner surface.

2. A kit according to claim 1, wherein the dentilated inner surface of the main slot of each fixator comprises a first plurality of dentilations, each tapering in a direction along the main slot which is away from the through hole thereof.

3. A kit according to claim 1, wherein the rigid planar member of each fixator is made of a radio-transparent material and the each external fixator further comprises a circular arc of radio-opaque material centered on the through hole thereof.

4. A kit according to claim 1, wherein the rigid planar member of each fixator further comprises a subsidiary slot connecting the parallel opposite sides of the respective fixator with each other, wherein the subsidiary slot extends away from the through hole, oblique to the main slot, and has a dentilated inner surface.

5. A kit according to claim 4, wherein the dentilated inner surface of the subsidiary slot of each fixator comprises a second plurality of dentilations, each tapering in a direction along the subsidiary slot thereof which is towards the main slot thereof.

6. A kit according to claim 4, wherein the subsidiary slot of each fixator is rectilinear.

7. A kit according to claim 4, wherein the rigid planar member of each fixator comprises a plurality of said subsidiary slots arranged parallel to each other.

8. A kit according to claim 7, wherein the rigid planar member of each fixator comprises two such pluralities of said subsidiary slots, wherein each of the two pluralities of subsidiary slots is arranged on opposite sides of the main slot thereof, the two pluralities of subsidiary slots are reflection-symmetric with each other about a line, and the main slot lies on the line.

9. A kit according to claim 2, wherein the dentilated inner surface of the main slot of each fixator comprises a third plurality of dentilations, located closer to the through hole thereof than the first plurality of dentilations and each tapering in a direction along the main slot of the respective fixator which is towards the through hole thereof.

10. A kit according to claim 1, wherein the rigid planar member of each fixator has a shape which is reflection-symmetric about a longitudinal axis, and the respective through hole and the main slot lie on the longitudinal axis thereof.

11. A kit according to claim 10, wherein:

the rigid planar member of each fixator is made of a radio-transparent material and each external fixator further comprises a circular arc of radio-opaque material centered on the through hole thereof; and in each fixator, each end of the arc of radio-opaque material defines a line subtending an angle with the longitudinal axis thereof in a range of angles from 100 to 140 degrees, inclusive.

12. A kit according to claim 1, wherein the rigid planar member of each fixator comprises a tail located at an opposite end of the main slot from the through hole thereof and connected to the rest of the rigid planar member by a neck of reduced width.

13. An external fixator according to claim 12, wherein the tail of each fixator has a deltoid or bifurcate shape and comprises a flat or concave surface at an opposite end of the rigid planar member from the through hole thereof.

14. An external fixator according to claim 3, wherein the arc of radio-opaque material is embedded within and enclosed by the rigid planar member.

15. A kit according to claim 1, wherein the pair of external fixators bear different indicia and/or have different colors from each other.

16. A kit according to claim 1, further comprising a plurality of Kirschner wires, wherein:

a first one of the Kirschner wires has a diameter which fits through the through hole in each of the pair of external fixators; and a second one of the Kirschner wires has a diameter which fits through the main slot in each of the pair of external fixators, but is restrained by the dentilated inner surfaces of the main slots from sliding freely along the main slots.

17. A kit according to claim 1, further comprising a stopper adapted to engage with the dentilated inner surface of the main slot in each of the pair of external fixators.

18. A kit according to claim 16, wherein:

in each of the pair of external fixators, the rigid planar member further comprises a subsidiary slot connecting the parallel opposite sides with each other, wherein the subsidiary slot extends away from the through hole, oblique to the main slot, and has a dentilated inner surface; and a third one of the Kirschner wires has a diameter which fits through the subsidiary slot in each of the pair of external fixators, but is restrained by the dentilated inner surfaces of the subsidiary slots from sliding freely along the subsidiary slots.

19. A kit according to claim 18, further comprising a stopper adapted to engage with the dentilated inner surface of the subsidiary slot in each of the pair of external fixators.

20. A kit according to claim 17, wherein the stopper comprises:

a cruciform head having arms joined to each other by circular arcs; and a body attached to the head;

wherein the body has a maximum width equal to a maximum separation between the respective dentilated inner surfaces of the main and subsidiary slots.

21. A kit according to claim 17, wherein the stopper is made of a thermoplastic material.

22. A kit according to claim 16, further comprising a container of adhesive for bonding at least one of the Kirschner wires to at least one of the pair of external fixators.

23. A kit according to claim 16, further comprising a Kirschner wire, pin or screw having a diameter which is greater than a width of the main slot in each of the pair of external fixators.

* * * * *